US008428217B2

(12) United States Patent
Peschmann

(10) Patent No.: US 8,428,217 B2
(45) Date of Patent: Apr. 23, 2013

(54) METHODS AND SYSTEMS FOR RAPID DETECTION OF CONCEALED OBJECTS

(75) Inventor: Kristian R. Peschmann, Torrance, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 12/946,513

(22) Filed: Nov. 15, 2010

(65) Prior Publication Data

US 2011/0228896 A1    Sep. 22, 2011

Related U.S. Application Data

(63) Continuation of application No. 12/047,472, filed on Mar. 13, 2008, now Pat. No. 7,856,081, which is a continuation of application No. 11/251,601, filed on Oct. 15, 2005, now Pat. No. 7,366,282, and a continuation-in-part of application No. 10/910,250, filed on Aug. 3, 2004, now abandoned, which is a continuation-in-part of application No. 10/662,778, filed on Sep. 15, 2003, now abandoned.

(60) Provisional application No. 60/619,339, filed on Oct. 15, 2004.

(51) Int. Cl.
*G01N 23/00*    (2006.01)

(52) U.S. Cl.
USPC ............................................... 378/5; 378/57

(58) Field of Classification Search .................. 378/4, 5, 378/6, 44–46, 57, 70–90
See application file for complete search history.

(56) References Cited

U.S. PATENT DOCUMENTS

| | | | |
|---|---|---|---|
| 2,831,123 | A | 4/1958 | Daly |
| 3,766,387 | A | 10/1973 | Heffan et al. |
| 3,784,837 | A | 1/1974 | Holmstrom |
| RE28,544 | E | 9/1975 | Stein et al. |
| 4,047,035 | A | 9/1977 | Dennhoven et al. |
| 4,139,771 | A | 2/1979 | Dennhoven et al. |
| 4,210,811 | A | 7/1980 | Dennhoven et al. |
| 4,216,499 | A | 8/1980 | Kunze et al. |
| 4,366,382 | A | 12/1982 | Kotowski |
| 4,430,568 | A | 2/1984 | Yoshida et al. |
| 4,566,113 | A | 1/1986 | Donges et al. |
| 4,599,740 | A | 7/1986 | Cable |
| 4,641,330 | A | 2/1987 | Herwig et al. |
| 4,736,401 | A | 4/1988 | Donges et al. |
| 4,754,469 | A | 6/1988 | Harding et al. |
| 4,788,704 | A | 11/1988 | Donges et al. |
| 4,789,930 | A | 12/1988 | Sones et al. |
| 4,825,454 | A | 4/1989 | Annis et al. |
| 4,884,289 | A | 11/1989 | Glockmann et al. |
| 4,956,856 | A | 9/1990 | Harding |
| 4,979,202 | A | 12/1990 | Siczek et al. |
| 4,991,189 | A | 2/1991 | Boomgaarden et al. |
| 5,007,072 | A | 4/1991 | Jenkins et al. |
| 5,008,911 | A | 4/1991 | Harding |

(Continued)

*Primary Examiner* — Jurie Yun
(74) *Attorney, Agent, or Firm* — Novel IP

(57) ABSTRACT

This specification is directed towards finding, locating, and confirming threat items and substances. The inspection system is designed to detect objects that are made from, but not limited to, special nuclear materials ("SNM") and/or high atomic number materials. The system employs a dual energy CT scanning first stage inspection system and advanced image processing techniques to analyze images of an object under inspection ("OUI"), which includes, but is not limited to baggage, parcels, vehicles and cargo.

20 Claims, 18 Drawing Sheets

U.S. PATENT DOCUMENTS

| | | |
|---|---|---|
| 5,022,062 A | 6/1991 | Annis |
| 5,065,418 A | 11/1991 | Bermbach et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis et al. |
| 5,263,075 A | 11/1993 | McGann et al. |
| 5,265,144 A | 11/1993 | Harding et al. |
| 5,313,511 A | 5/1994 | Annis et al. |
| 5,367,552 A | 11/1994 | Peschmann |
| 5,379,334 A | 1/1995 | Zimmer et al. |
| 5,420,905 A | 5/1995 | Bertozzi |
| 5,493,596 A | 2/1996 | Annis |
| 5,524,133 A | 6/1996 | Neale et al. |
| 5,600,303 A | 2/1997 | Husseiny et al. |
| 5,600,700 A | 2/1997 | Krug et al. |
| 5,638,420 A | 6/1997 | Armistead |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,692,028 A | 11/1997 | Geus et al. |
| 5,745,543 A | 4/1998 | De Bokx et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,974,111 A | 10/1999 | Krug et al. |
| 6,031,890 A | 2/2000 | Bermbach et al. |
| 6,054,712 A | 4/2000 | Komardin et al. |
| 6,058,158 A | 5/2000 | Eiler |
| 6,067,344 A | 5/2000 | Grodzins et al. |
| 6,081,580 A | 6/2000 | Grodzins et al. |
| 6,094,472 A | 7/2000 | Smith |
| 6,118,850 A | 9/2000 | Mayo et al. |
| 6,128,365 A * | 10/2000 | Bechwati et al. ............... 378/57 |
| 6,151,381 A | 11/2000 | Grodzins et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,218,943 B1 | 4/2001 | Ellenbogen |
| 6,249,567 B1 | 6/2001 | Rothschild et al. |
| 6,252,929 B1 | 6/2001 | Swift et al. |
| 6,256,369 B1 | 7/2001 | Lai |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,320,933 B1 | 11/2001 | Grodzins et al. |
| 6,356,620 B1 | 3/2002 | Rothschild et al. |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,453,003 B1 | 9/2002 | Springer et al. |
| 6,453,007 B2 | 9/2002 | Adams et al. |
| 6,456,684 B1 | 9/2002 | Mun et al. |
| 6,459,761 B1 | 10/2002 | Grodzins et al. |
| 6,459,764 B1 | 10/2002 | Chalmers |
| 6,473,487 B1 | 10/2002 | Le |
| RE37,899 E | 11/2002 | Grodzins et al. |
| 6,483,894 B2 | 11/2002 | Hartick et al. |
| 6,507,025 B1 | 1/2003 | Verbinski et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,563,903 B2 | 5/2003 | Kang et al. |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,628,745 B1 | 9/2003 | Annis et al. |
| 6,636,581 B2 | 10/2003 | Sorenson |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,665,433 B2 | 12/2003 | Roder |
| 6,798,863 B2 | 9/2004 | Sato |
| 6,812,426 B1 | 11/2004 | Kotowski et al. |
| 6,816,571 B2 | 11/2004 | Bijjani et al. |
| 6,837,422 B1 | 1/2005 | Meder |
| 6,839,403 B1 | 1/2005 | Kotowski et al. |
| 6,922,460 B2 | 7/2005 | Skatter et al. |
| 6,928,141 B2 * | 8/2005 | Carver et al. ................... 378/57 |
| 7,092,485 B2 | 8/2006 | Kravis |
| 7,207,713 B2 | 4/2007 | Lowman |
| 7,322,745 B2 | 1/2008 | Agrawal et al. |
| 7,369,643 B2 | 5/2008 | Kotowski et al. |
| 2004/0141584 A1 | 7/2004 | Bernardi et al. |
| 2005/0180542 A1 | 8/2005 | Leue et al. |

* cited by examiner

| Z, Element | X-ray lines in keV | | | | |
|---|---|---|---|---|---|
| 26 Iron | 6.4; 7 | 73 Tantalum | 57.5; 65.2 | 79 Gold | 68.8; 78 |
| 27 Cobalt | 6.9; 7.6 | 74 Tungsten | 59.3; 67.2 | 82 Lead | 75; 84.9 |
| 50 Tin | 25.3; 28.5 | 78 Platinum | 68.8; 75.7 | 92 Uranium | 98.4; 111.3 |
| | | | | 94 Plutonium | |

FIG. 16

METHODS AND SYSTEMS FOR RAPID DETECTION OF CONCEALED OBJECTS

CROSS-REFERENCE TO RELATED APPLICATIONS

The present application is a continuation of U.S. patent application Ser. No. 12/047,472 filed on Mar. 13, 2008, now issued as U.S. Pat. No. 7,856,081, which is a continuation of U.S. patent application Ser. No. 11/251,601 filed on Oct. 15, 2005, now issued as U.S. Pat. No. 7,366,282, which relies on U.S. Provisional Patent No. 60/619,339, filed on Oct. 15, 2004, for priority and is a continuation-in-part of U.S. patent application Ser. No. 10/910,250, filed on Aug. 3, 2004, abandoned, which is a continuation-in-part of U.S. patent application Ser. No. 10/662,778, filed on Sep. 15, 2003, abandoned.

FIELD OF THE INVENTION

The present invention relates generally to X-ray based methods and systems for detection of concealed threats, and threat resolution, and more specifically to improved methods and systems, for the detection of concealed threats, such as explosives. Optionally, the present invention uses a multiple stage scanning system to process luggage for the detection of concealed threats.

BACKGROUND OF THE INVENTION

Conventional X-ray systems produce radiographic projection images, which are then interpreted by an operator. These radiographs are often difficult to interpret because objects are superimposed. A trained operator must study and interpret each image to render an opinion on whether or not a target of interest, a threat, is present. With a large number of such radiographs to be interpreted, and with the implied requirement to keep the number of false alarms low, operator fatigue and distraction can compromise detection performance.

Advanced technologies, such as dual-energy projection imaging and Computed Tomography (CT), are being used for contraband detection, in addition to conventional X-ray systems. In dual-energy imaging, the effective atomic numbers of materials in containers are measured. However, the dual-energy method does not readily allow for the calculation of the actual atomic number of the concealed 'threat' itself, but rather yields only an average atomic number that represents the mix of the various items falling within the X-ray beam path, as the contents of an actual luggage is composed of different items and rarely conveniently separated. Thus dual-energy analysis is often confounded. Even if the atomic number of an item could be measured, the precision of this measurement would be compromised by X-ray photon noise to the extent that many innocuous items would show the "same" atomic number as many threat substances, and therefore the atomic number in principle cannot serve as a sufficiently specific classifier for threat versus no threat.

In X-ray CT cross-sectional images of slices of an object are reconstructed by processing multiple attenuation measurements taken at various angles around an object. CT images do not substantially suffer from the super-positioning problem present in standard radiographs. However, conventional CT systems take considerable time to perform multiple scans, to capture data, and to reconstruct the images. The throughput of CT systems is generally low. Coupled with the size and expense of CT systems this limitation has hindered CT use in applications such as baggage inspection where baggage throughput is an important concern. In addition, CT alarms on critical mass and density of a threat, but such properties are not unique to explosives. CT based systems suffer from high false alarm rate. Any such alarm is then to be cleared or confirmed by an operator, again interpreting images, or hand searching.

Apart from X-ray imaging systems, detection systems based on X-ray diffraction, or coherent scatter are also known. Their primary purpose is not to acquire images but to obtain information about the molecular structure of the substances an object is composed of. The so-called diffraction or coherent scatter signature is based on BRAGG reflection that is the interference pattern of X-ray light, which develops when X-rays are reflected by the molecular structure or electron density distribution of a substance. The resulting diffraction spectra can be analyzed to determine the molecular structure of the diffracting object, or at least to recognize similarity with any one of a number of spectra, which have previously been obtained from dangerous substances.

One approach to detecting explosives in luggage was disclosed in British patent No. 2,299,251 in which a device uses Bragg reflection from crystal structures to identify crystalline and poly-crystalline substances. Substances can be identified because the energy spectrum distribution of the polychromatic radiation reflected at selected angles is characteristic of the crystal structure of the substance reflecting the radiation.

U.S. Pat. Nos. 4,754,469, 4,956,856, 5,008,911, 5,265,144, 5,600,700 and 6,054,712 describe methods and devices for examining substances, from biological tissues to explosives in luggage, by recording the spectra of coherent radiation scattered at various angles relative to an incident beam direction. U.S. Pat. No. 5,265,144 describes a device using concentric detecting rings for recording the radiation scattered at particular angles. Each of the prior art systems and methods, however, suffer from low processing rates because the scatter interaction cross sections are relatively small and the exposure times required to obtain useful diffraction spectra are long, in the range of seconds and minutes. For security inspections, equipment performance has to combine high detection sensitivity and high threat specificity with high throughput, at the order of hundreds of bags per hour.

U.S. Pat. No. 5,182,764 discloses an apparatus for detecting concealed objects, such as explosives, drugs, or other contraband, using CT scanning. To reduce the amount of CT scanning required, a pre-scanning approach is disclosed. Based upon the pre-scan data, selected locations for CT scanning are identified and CT scanning is undertaken at the selected locations. Here, CT scanning is used as the secondary scan.

U.S. Pat. No. 5,642,393, assigned to Vivid Technologies, Inc., discloses "an inspection system for detecting a specific material of interest in items of baggage or packages, comprising: a multi-view X-ray inspection probe constructed to employ X-ray radiation transmitted through or scattered from an examined item to identify a suspicious region inside said examined item; said multi-view X-ray inspection probe constructed to identify said suspicious region using several examination angles of said transmitted or scattered X-ray radiation, and also constructed to obtain spatial information of said suspicious region and to determine a geometry for subsequent examination; an interface system constructed and arranged to receive from said X-ray inspection probe data providing said spatial information and said geometry; a directional, material sensitive probe connected to and receiving from said interface system said spatial information and said geometry; said material sensitive probe constructed to acquire material specific information about said suspicious region by employing said geometry; and a computer constructed to process said material specific information to identify presence of said specific material in said suspicious region."

In addition, various passive systems have been employed to detect explosives and specific materials in an object. For example, U.S. Pat. No. 5,007,072 discloses "a method of inspecting parcels to detect the presence of selected crystalline materials in the presence of other crystalline and non-crystalline materials comprising: generating x-ray radiation from a source; conveying a parcel containing crystalline and non-crystalline materials to be inspected continuously past the source to irradiate the materials with the radiation; detecting radiation scattered by crystalline material within the parcel at a predetermined angle; and analyzing a spectrum of the detected radiation to detect the presence of a selected crystalline material on or within the parcel."

The above systems do not however, effectively detect high atomic number ("High-Z") materials. Detecting such materials, particularly smuggled special nuclear materials ("SNM") that could potentially be used to make a weapon, is much more complex task. One of the materials of greatest concern, highly enriched uranium ("HEU"), has a relatively low level of radioactivity. Plutonium, yet another nuclear weapons grade material, has a higher specific activity and higher energy emissions. However, it can also be easily shielded by employing a combination of a high-atomic-number ("high-Z") material for shielding gamma rays and a low atomic number ("low-Z") neutron absorber for shielding the neutrons produced by spontaneous fission events. Thus, it is very difficult to detect shielded or concealed materials.

Because typical radioactive sources used in a radiological dispersal device ("dirty bomb") are physically very small but have high specific activities, they must be shielded for safe handling which prevents their detection via well-known passive techniques. For example, an industrial Co-60 source may contain 30,000 Ci in pellet form, wherein the total combined weight of the pellets is only about 100 grams. Reducing the exposure rate from this source, and as a result, below the detection limits of portal monitors requires a lead shield that is about 40 cm thick and weighing about 5,000 kg.

High atomic number ("High-Z") screening is feasible due to the high absorption of X-rays and gamma rays by special nuclear materials and gamma-ray shielding materials, such as lead and tungsten. This is a consequence of their high density and atomic number (specifically, 74 for Tungsten, 82 for Lead, 92 for Uranium, and 94 for Plutonium). These materials are not commonly found within the "normal" stream-of-commerce, characterized primarily by goods composed of low atomic number "low-Z" and "intermediate-Z" elements. Low-Z goods include furniture, produce, clothing, liquids, plastics and other items made from constituents whose atomic numbers range from 5 to 10 (i.e. Carbon to Oxygen). Intermediate-Z goods include machinery, vehicles, and other items made from constituents whose atomic numbers range from 13 to 26 (i.e. Aluminum, Steel).

Accordingly, there is still a need for an improved high z material and explosive threat detection system that captures data through an X-ray system and utilizes this data to identify threat items in a rapid, yet accurate, manner. Further, there is a need for a system that is highly threat specific for reliably and automatically discerning threats from innocuous materials and items while still being able to process in excess of 100 bags per hour. Further, there is a need for a system that utilizes relatively inexpensive industrial components, and does not need special support facilities. Additionally, there is a need for a system that provides for greater accuracy in utilizing scan data to identify an inspection region and in processing scan data.

SUMMARY OF THE INVENTION

One object of the present invention is to provide for an improved scanning process having a first stage to pre-select the locations of potential threats and a second stage to accurately identify the nature of the threat. The improved scanning process increases throughput by limiting the detailed inspection to a small fraction of the total bag volume.

Another object of the invention is to provide for improved processing techniques performed in association with various scanning systems. Another object of the invention is to provide for a method and system to screen for relatively small amounts of threat material. Another object of the invention is to provide for an improved method and system for screening for explosives in the form of thin sheets.

Another object of the invention is to provide a screening solution at low cost by utilizing standard industrial components, including relatively low cost and rugged industrial X-ray systems and detector systems.

Accordingly, one embodiment of the present invention provides an apparatus for identifying an object concealed within a container. These objects may be considered threats, such as an illegal drug, an explosive material, or a weapon. The apparatus for identifying an object concealed within a container comprises a first stage inspection system having an X-ray scanning system to generate a first set of data, a plurality of processors in data communication with the first stage inspection system wherein the processors process said first set of data and wherein the first set of data is used to identify at least one target region; a means for positioning an inspection region relative to the target region wherein an inspection region at least partially physically coincides with the target region; and a second stage inspection system for generating the inspection region wherein the second stage inspection system produces a second set of data having an X-ray signature characteristic and/or fluorescence signature characteristic of the material in said inspection region.

Optionally, the apparatus further comprises a bypass conveyor capable of moving said object into a secured area without first passing through said second stage inspection system. Optionally, the operator selects a region based upon an X-ray characteristic. The X-ray characteristic is at least one of mass, degree of attenuation, area, atomic number, size, shape, pattern, or context. The target region can also be identified by having a processor execute an algorithm to select a region based upon said first set of data. Optionally, the apparatus has a plurality of X-ray beam projections intersecting the target region at an intersection area. The location of the target region is determined by identifying a set of coordinates for the intersection area.

In another embodiment, the present invention is directed towards a method for identifying an object concealed within a container, comprising the steps of generating a first set of data using a first stage X-ray inspection system; processing said first set of data using a plurality of processors in data communication with the first stage inspection system; identifying at least one target region from said processed first set of data; positioning an inspection region relative to the target region wherein the inspection region at least partially physically coincides with the target region; generating the inspection region through a second stage inspection system; and producing a second set of data having a X-ray signature characteristic and fluorescence signature characteristic of the material in the inspection region.

In another embodiment, the present invention comprises a single stage inspection system comprising an X-ray diffraction and fluorescence diffraction system. Contraband, high z or other illegal material located within a target object is identified using a radiation source by passing a target object into a C-shaped inspection system; directing an X-ray beam from said radiation source toward a target object; detecting a diffraction signal using a diffraction detector head; detecting a fluorescence signal using a fluorescence detector head; and identifying contraband material using said diffraction signal and said fluorescence signal. The method can further comprise the steps of: generating an image of said target object; analyzing the image using an algorithm to evaluate regions of objects based upon a threshold level; segmenting said image into regions based upon criteria; further inspecting selected regions satisfying certain criteria to determine their size and shape; comparing said selected regions to threat criteria; and issuing an alarm to an inspector when an object is determined as matching said threat criteria in said comparing step.

In another embodiment, the present invention is a device for identifying target material located within a target object using a radiation source, comprising a first member having detector electronics and a diffraction detector head; a second member affixed substantially perpendicularly to the first member; a third member affixed substantially perpendicularly to the second member and parallel to the first member, wherein the third member comprises a radiation source for projecting an X-ray beam toward the target object and comprises a fluorescence detector head; and a conveyor for positioning said target object between said first member and said second member. The device can operate by detecting a diffraction signal using a diffraction detector head; detecting a fluorescence signal using a fluorescence detector head; and identifying said material using said diffraction signal and said fluorescence signal.

The device comprises at least one processor and display for generating an image of said target object; at least one processor having software for analyzing the image using an algorithm to evaluate regions of objects based upon a threshold level; at least one processor having software for segmenting said image into regions based upon criteria; at least one processor having software for directing the device to further inspect selected regions satisfying certain criteria to determine their size and shape; at least one processor having software for comparing said selected regions to threat criteria; and at least one processor having software for issuing an alarm to an inspector when an object is determined as matching said threat criteria in said comparing step.

Accordingly, one embodiment of the present invention comprises a first stage X ray inspection system that scans a container at a plurality of projections to generate a first set of data comprising the attenuation scan data of the container under inspection and a data processing system in data communication with the first stage inspection system. The processors process the first set of data to generate at least a plurality of image maps of the container, coded in gravimetric density. The images are then subjected to a set of image interpretation algorithms, also processed by the processors, to identify target regions in the images and also generate a three dimensional image map of the container to be displayed on a monitor. Since the images are projected in different direction it is possible to back-project identified target regions and to locate those targets in system coordinates.

The first stage inspection system therefore locates potential threat items, regions, and/or areas, based on X-ray images, manual or automatic detection algorithms, and triangulation. The second stage inspection system then focuses on the identified items, regions, and/or areas to produce characteristic signatures which are then used to determine whether a threat is, in fact, present.

In one embodiment, a target region is identified from the images generated in the first stage inspection system by having an operator select a particular region displayed in the images. In a preferred embodiment, the operator directs a cursor, using an interface, such as a mouse, to position crosshairs on each of the two images. The two crosshairs determine a certain location in system coordinates. The selection for the cross hair location may occur based upon an X-ray image characteristic, such as the X-ray shadow of an object, seen in both images. Optionally, the target selection process may be performed electronically. Target regions are identified from the two images by having a processor execute an algorithm to select regions in the images, which correspond to objects or mass accumulations. With the locations of each of the two images determined, the coordinates corresponding to the physical locations of the target region can be determined and used to direct the system, and, in particular, the conveyor.

Once the target region is determined, either through automatic or operator processing means, a plurality of control commands is produced and used to position, by a multiple-axis motion control system, the second stage inspection system such that an inspection region, at least partially, coincides with the determined target coordinates. In one embodiment, the inspection region is positioned relative to the target region using a plurality of adjustable apertures that can be physically moved. The apertures can be ring-shaped with an adjustable diameter. Optionally, the means for positioning the inspection volume relative to the target region comprises a motion-controlled conveyor operable to move in elevation as well as back and forth relative to the second stage inspection system. Optionally, the inspection region can be moved across the conveyor by mounting the second stage inspection system on a C-arm which is motion controlled to move back and forth across the conveyor, or alternatively by employing a parallel set of fixed linear bearings and synchronized linear motion to effect the same relative movement.

The second stage inspection system generates an inspection volume in space and produces a second set of data having an X-ray signature and/or fluorescence signature characteristic of the material in that inspection volume. The X-ray signature characteristic is a diffraction pattern, also called scatter spectrum, and an intensity level associated with that spectrum, and, in addition, a set of dual energy transmission measurements in close proximity to the ray path of the diffraction measurement.

The second stage inspection system comprises a source of X-ray radiation. In one embodiment, it comprises an energy dispersive detector. In another embodiment, it comprises an array of transmission detectors. In another embodiment, it comprises an array of fluorescence detectors. The energy dispersive detector is used to produce a signature of the material in the inspection region and the array of transmission detectors is used to produce data defining at least one of mass, degree of attenuation, area, and average atomic number, of the material in a beampath. Optionally, the array of transmission detectors is in a ring formation. In a preferred embodiment, the array of transmission detectors comprises high energy and low energy detectors. Data generated from the transmission detectors is used to determine a reference spectrum by identifying a spectrum associated with data generated from both the high energy detectors and the low energy detectors. The reference spectrum can be used to correct a diffraction spectrum or to correct for beam hardening.

In one embodiment, the present invention comprises a first stage inspection system having a scanning system to generate a first set of data; a plurality of processors in data communication with the first stage inspection system wherein the processors process said first set of data and wherein the first set of data is used to identify at least one target region; a means for positioning an inspection region relative to the target region wherein an inspection region at least partially physically coincides with the target region; and a second stage inspection system for generating the inspection region wherein the second stage inspection system produces a second set of data having an X-ray signature characteristic of the material in said inspection region and a third set of data having an fluorescence signature characteristic of the material in said inspection region.

Optionally, the second stage inspection system is a C-shaped inspection system. The second stage inspection system comprises at least one diffraction detector head and at least one fluorescence detector head. The apparatus further comprises a bypass conveyor capable of moving said object into a secured area without first passing through said second stage inspection system. An operator selects a region based upon an X-ray characteristic. The X-ray characteristic is at least one of mass, degree of attenuation, area, atomic number, size, shape, pattern, or context. The target region is identified by having a processor execute an algorithm to select a region based upon said first set of data.

Optionally, a plurality of X-ray beam projections intersects the target region at an intersection area, said target region having a location. The location of the target region is determined by identifying a set of coordinates for the intersection area. A plurality of control commands is produced in response to the determination of said location of the target region. The inspection region is positioned relative to the target region in response to the plurality of control commands using a three-axis control system.

Optionally, the means for positioning said inspection region relative to the target region includes a plurality of adjustable apertures. The apertures can be physically moved in the direction of the main beam axis. The aperture is a ring aperture having an adjustable diameter. The means for positioning said inspection region relative to the target region comprises a conveyor operable to move in elevation relative to the second stage inspection system. The means for positioning said inspection region relative to the target region comprises an aperture and ring aperture. The second stage inspection system comprises an inspection region generation system. The inspection region generation system comprises a source of X-ray radiation.

Optionally, the inspection region generation system comprises an energy dispersive detector. The energy dispersive detector is used to produce a signature of the material in the inspection region. The inspection region generation system comprises a fluorescence detector. The fluorescence detector is used to produce a signature of the material in the inspection region. The first set of data is used to identify a reference spectrum. The identification of a reference spectrum is achieved by identifying a spectrum associated with said first set of data. The reference spectrum is used to correct a diffraction spectrum. The reference spectrum is used to correct for beam hardening. The X-ray signature characteristic is a diffraction pattern. The X-ray signature characteristic is a scatter spectrum. The X-ray signature characteristic is an electronic response signal.

In another embodiment, the present invention is a device for inspecting high atomic number material located within a target object using a radiation source, comprising: a first member having detector electronics and a diffraction detector head; a second member affixed substantially perpendicularly to the first member; a third member affixed substantially perpendicularly to the second member and parallel to the first member, wherein the third member comprises a radiation source for projecting an X-ray beam toward the target object and comprises a fluorescence detector head; and a conveyor for positioning said target object between said first member and said second member.

The device operates by detecting a diffraction signal using a diffraction detector head; detecting a fluorescence signal using a fluorescence detector head and identifying said high atomic number material using said diffraction signal and said fluorescence signal. Optionally, the device further comprises at least one processor and display for generating an image of said target object; at least one processor having software for analyzing the image using an algorithm to evaluate regions of objects based upon a threshold level; at least one processor having software for segmenting said image into regions based upon criteria; at least one processor having software for directing the device to further inspect selected regions satisfying certain criteria to determine their size and shape; at least one processor having software for comparing said selected regions to threat criteria; and at least one processor having software for issuing an alarm to an inspector when an object is determined as matching said threat criteria in said comparing step.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following Detailed Description when considered in connection with the accompanying drawings, wherein:

FIG. 6 is a schematic diagram of a C-arm structure of one embodiment of the present invention;

FIG. 16 is a table showing the K-shell fluorescence line energies in keV of a selection of different materials;

DETAILED DESCRIPTION OF THE INVENTION

The methods and systems described herein are directed towards finding, locating, and confirming threat items and substances. Such threats may comprise high z materials and explosives such as C4, RDX, Semtex, Seismoplast, PE4, TNT, dynamite, PETN, ANFO among others, as well as other contraband such as drugs. Although the embodiments have been described in the context of a baggage inspection system, it should be evident to persons of ordinary skill in the art that items other than luggage such as other packages, mail, and cargo-containers, or even processed food stuffs, can also be analyzed and screened or graded and that the descriptions are exemplary and are not restrictive of the invention. Further, while the invention is described as a dual-stage system and method, any of the processing techniques discussed herein can be applied to each of the individual scanning stages.

Figure 1:
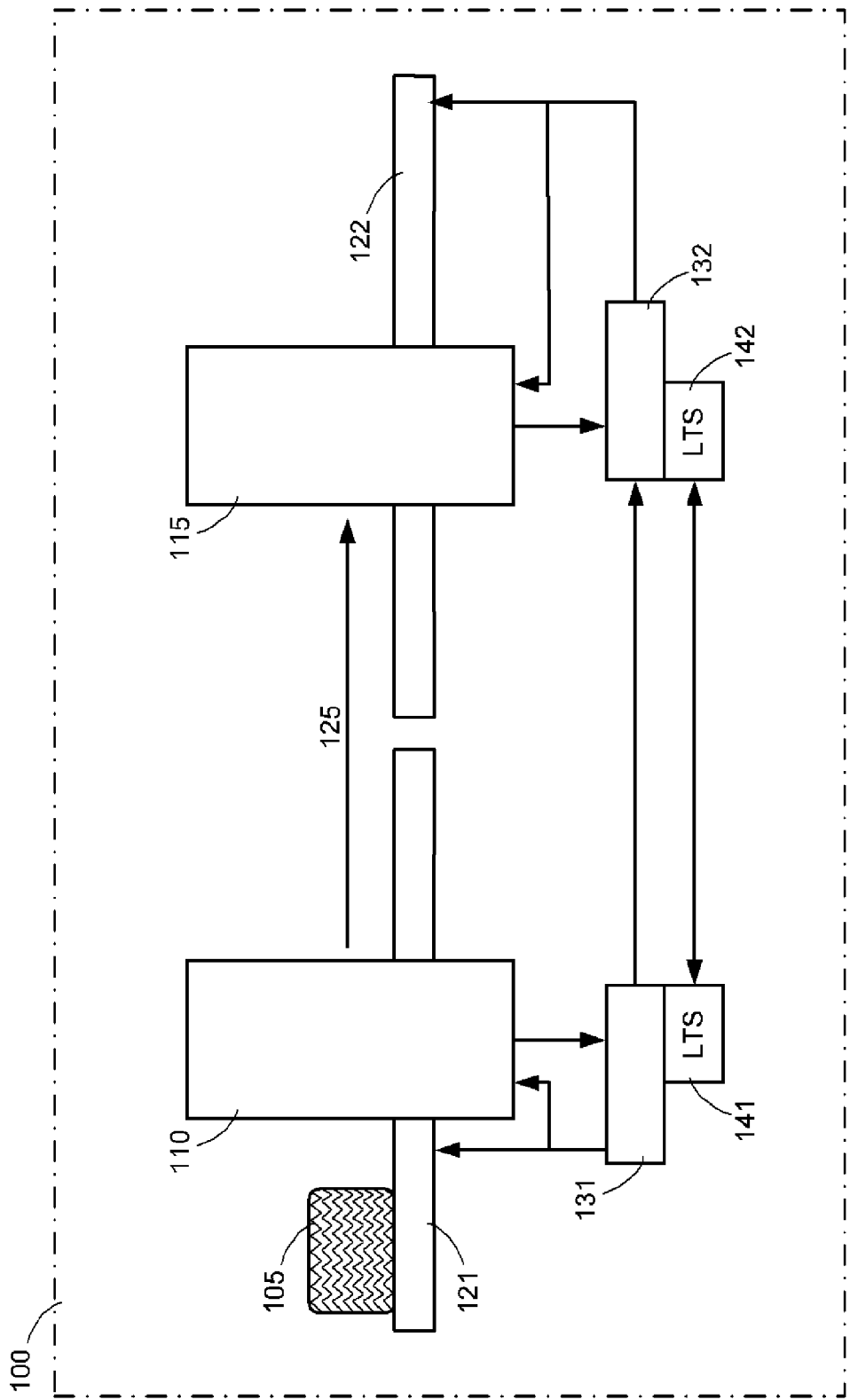
FIG. 1 is a block diagram depicting the dual stage X-ray scanning system as used in one embodiment of the present invention.

Referring to FIG. 1, a dual stage scanning system 100 comprises conveyor systems 121, 122 for moving containers, baggage, luggage, or similar object 105 through a plurality of scanning stages 110, 115. In one embodiment, dual stage X-ray scanning system 100 comprises a X-ray scanning unit as a first stage 110 and a Substance-Identification Unit (S-I Unit) as a second stage 115. In an exemplary embodiment object 105 is, but is not limited to, a piece of baggage and will be described as such hereinafter. Baggage 105 moves through the two stages via conveyor systems 121, 122 in the direction of arrow 125 (along the X-axis). Conveyor systems 121,122 are controlled and coordinated by Luggage Transport Subsystems (LTS) 141, 142, respectively, thus operating the combined system 100 at a high-duty cycle. Both the first stage and second stage further comprise computer processing systems 131 and 132, for respectively receiving and processing, X-ray data signals and small angle X-ray diffraction spectra and fluorescence spectra of a threat location. Optionally, a bypass conveyor belt is provided between the first stage 110 and second stage scanning units 115 that enables the object 105 to be passed through the scanning system without having to be first inspected by the second stage scanning unit 115. Such a bypass can be used if the first stage scanning unit 110 indicates that no threat exists, or no suspicious region exists, in the object 105 based on the first stage scan.

In one embodiment, first stage 110 is a CT unit or X-ray transmission unit, generating imaging data, coded in gravimetric density. Computer processing system 131 of the first stage 110, generates automatic image analysis resulting in, but not limited to, the approximate shape, size, density, weight and, location of potential threats. As the piece of baggage 105 is transported into second stage 115 via conveyor system 122 along arrow 125, the computer processing system 132 of the S-I Unit receives a map of the threats. Processing system 132 also receives the image volume file from the X-ray scanning or CT Unit via suitable transmission links, such as, but not limited to an Ethernet LAN (Local Area Network) connection.

The S-I Unit subsequently interprets the map of threats and image volume data in second stage 115 and reacts by moving its probing beams into the position best suited for sampling the threat resolution information. In second stage 115, based upon its automatic threat resolution algorithm, the S-I Unit provides data to an operator who can manually activate an alarm or clear an object, or, based on the data, the system can automatically clear the objector activate an alarm.

Figure 2:
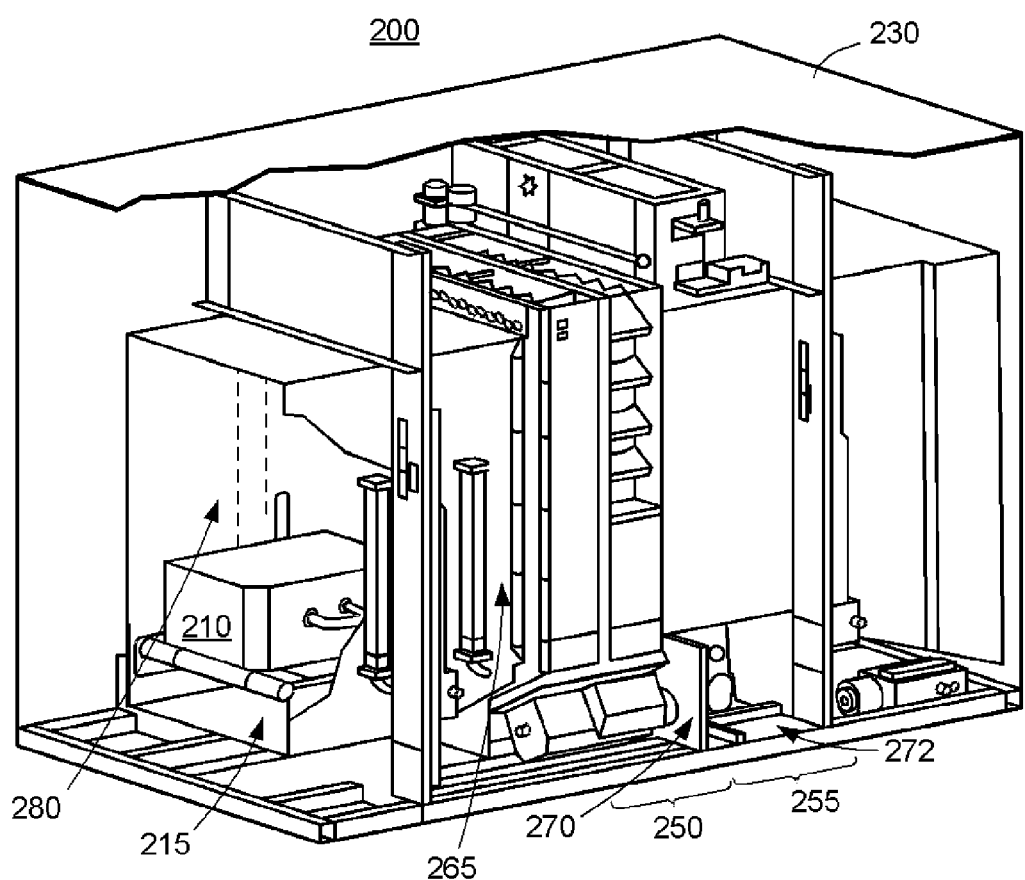
FIG. 2 is a schematic view of one embodiment of the dual stage X-ray scanning system.

Referring to FIG. 2, a dual stage scanning system 200 comprises a housing 230, which encompasses a conveyor system 215 for moving containers, baggage, luggage, or similar object 210 through a plurality of scanning stages 250, 255. A sensor system 265 is connected at the entrance to determine when an object being scanned 210 enters the scan field and communicates with a controller [not shown] to activate or deactivate an X-ray radiation source, 270, 272, as needed. A lead lined tunnel 280 surrounds the conveyor to reduce radiation leakage outside the equipment. At least one radiation source is not expressly depicted in FIG. 2 and would be visible if the system were viewed from the opposite side.

Figure 3:
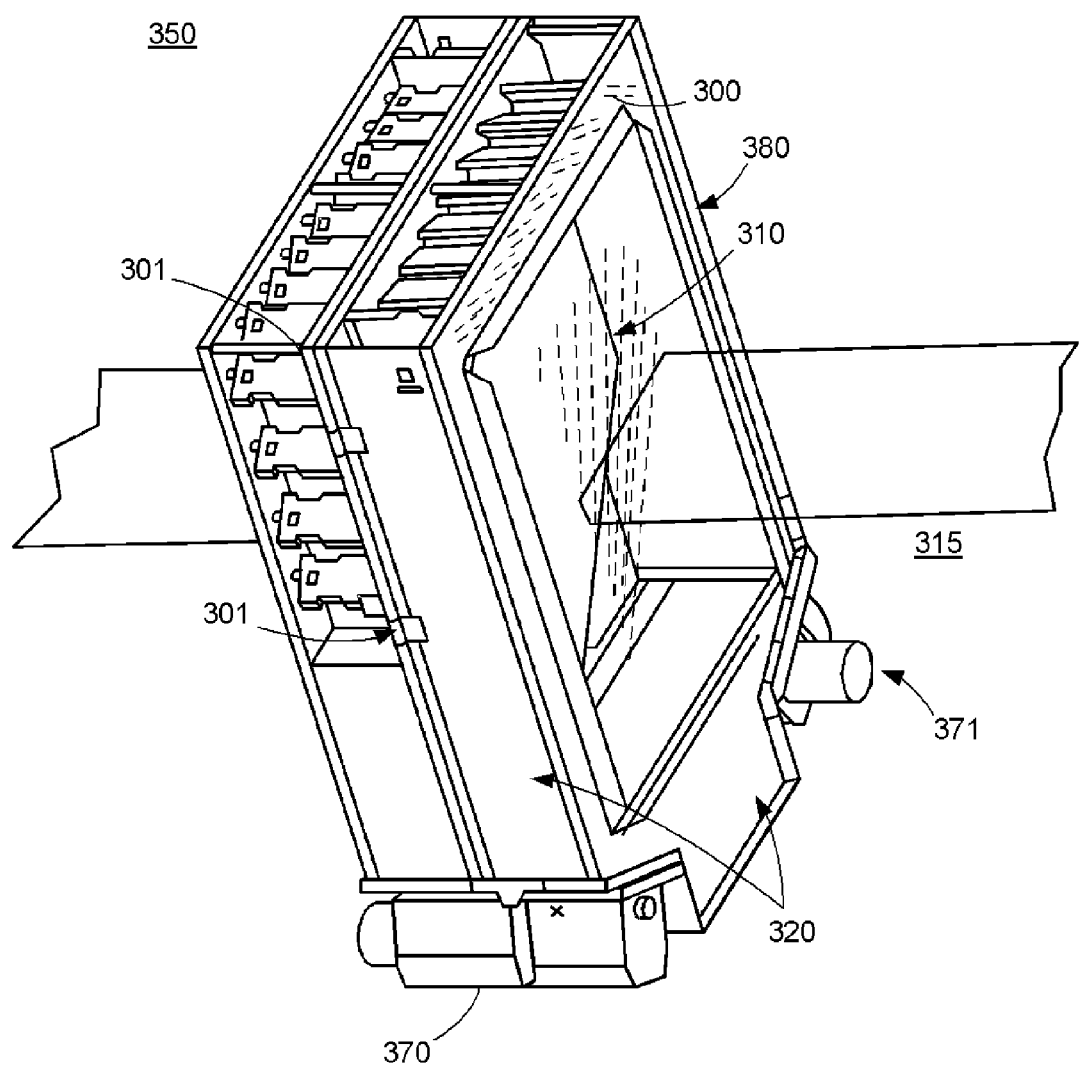
FIG. 3 is a schematic view of one embodiment of an X-ray scanning system for the first stage scanning system.

Referring to FIG. 3, the first stage 350, comprises two X-ray cameras held together by a support structure 320, such as a frame or yoke, for stability. Each camera consists of an X-ray source 370, 371, a X-ray focusing means, such as a collimating slit comprised of a radio-opaque material, for example lead (not shown), and an array of detectors, 300, 301. In one embodiment, it is preferred that the detectors are configured into a L-shape in order to save space. One of ordinary skill in the art would appreciate that other folded configurations may be acceptable, provided that the detectors are appropriately positioned relative to the inspection region and X-ray source.

Behind each slit collimator, a thin sheet of X-rays 310 is formed. Within the sheet, a fan of pencil beams can be defined, shown as dashed lines in FIG. 3, by connecting lines between the stationary focus, not shown, and channels in the detector array. Between focus and detector is a tunnel 380 through which the luggage is transported or moved using any means known in the art, including, for example, a conveyor 315, the surface of which is depicted in FIG. 3. Wherever in the system radiation has to be transmitted from X-ray sources 370, 371 and through the region defined by tunnel 380, the conveyor belt support structure as well as the tunnel has windows constructed from materials essentially translucent to X-rays. The collimating slits and detector arrays are oriented so that the radiation-fans intersect the main conveyor surface within a few degrees of perpendicular relative to the conveyor surface. The two X-ray sources and their fans point in different directions.

In one embodiment, the detector arrays are mounted on printed circuit boards with a vector positioned normal to their surfaces directed to the X-ray focus. An exemplary printed circuit board has a capacity of 64 channels, and the boards are physically arranged in Venetian blind configuration. The detector arrays consist of linear arrays of silicon photodiodes that are covered with scintillation material, which produces light when exposed to X-rays. The light is detected by the photodiodes that produce corresponding photo current signals. The detectors measure to what degree the X-ray signal has attenuated due to passing through a defined inspection volume. Specifically, the detected data are converted to digital format, corrected for detector gain and offset, and then stored. The required processor means may comprise computing hardware, firmware and/or software known to persons of ordinary skill in the art. When a container under inspection is moving through the tunnel and passing through the X-ray projections, both detector arrays are being sampled repetitively between 50 and 500 times per second. Displaying the line projections on a monitor renders the projection X-ray image.

While a conventional line scan system could be used as the first stage scanning system, it is preferred to use the system as described herein. More specifically, the present invention provides for the placement of at least two X-ray sources such that the directions of the X-ray projections emanating from the sources are mirrored relative to the central vertical plane. Therefore, from the perspective of a view along the path of conveyance through the first stage scanning system, at least one X-ray generator is mounted at a five o'clock position and at least one X-ray generator is mounted at the 7 o'clock position.

One of ordinary skill in the art would appreciate that the first stage scanning system is not limited to the specific embodiments described above and that other variations are included within the scope of this invention. In one alternative embodiment, detector arrays are expanded from a single array to multiple parallel arrays of detectors. In a second alternative embodiment, X-ray projections are taken using two-dimensional pixellated detector planes, without requiring the use of a conveyance means. It should be appreciated that, while the present invention will be further described using a description of the invention based on using the line scan configuration of single stationary foci and single line detector arrays in conjunction with a means of conveyance, the present invention includes other systems and methods that generate X-ray projection images and that such systems and methods can be used in the novel dual stage scanning system disclosed herein.

An alternative embodiment uses dual energy imaging. Dual energy imaging can be utilized to display an image where materials of a metallic constituency are suppressed (not displayed) or materials of an organic constituency are suppressed. Having the ability to selectively display certain materials within images helps reduce image clutter. For example, when inspecting containers for masses or explosives, which have little or no metallic component, the "organic materials only" display is preferred. The dual energy approach can be further refined to automatically discriminate between similar materials of higher and lower relative atomic numbers, such as between a plastic comprised of more lower atomic number atoms like hydrogen and carbon and a plastic comprised of more higher atomic number elements like oxygen and nitrogen; or between aluminum (atomic number 13) and steel (atomic number 26).

In one embodiment, dual energy data is generated by using an X-ray tube with extended spectral emission, which is standard, in conjunction with arrays of stacked detectors, where the first detector is positioned to detect more of the lower energy, or so-called softer X-ray photons, and the second detector is positioned to detect the balance of the energy, namely the higher energy, or so-called harder, photons. The second detector is typically positioned behind the first detector. The low energy and high energy measurements are combined in a suitable way using a series of calibration measurements derived from dual energy measurements taken of identified organic and metallic materials of known thicknesses and result in the display of images, including organic only or metal only images. One of ordinary skill in the art would appreciate that various dual energy line scan systems are commercially available.

It is preferred to use projection imaging as the first stage scanning step in this invention. Features shown in the projection images can be used by an operator to make a final decision on whether items identified in a container represent a threat of some type. Additionally, by taking projections from at least two different angles, it is possible to triangulate the location of a potential threat relative to the physical coordinates of the system and use those coordinates to perform a more specific and focused second stage scan. The triangulation process localizes certain items that generate features of interest in the images and identifies their location in the form of system coordinates.

To perform the triangulation process, the images that form the basis of the triangulation process and that are used to identify a target region are first identified. In one embodiment, the images are analyzed by an operator who visually and approximately determines a plurality of X-ray image characteristics, such as degree of attenuation and projected area, associated with mass, atomic number (identified using image color coding), and shape. Operators also use contextual information, such as an X-ray opaque organic mass in a transistor radio or a suspiciously thick suitcase wall. The analytical process is known to those of ordinary skill in the art and includes the interpretation of X-ray image characteristics.

In another embodiment, images are identified by determining the target regions automatically. For example, where the screening target is a mass of plastic explosive, known algorithms, working on dual energy X-ray projection image data, can be combined to automatically find such target. Examples for such algorithm components include, but are not limited to, edge detection, watershed, and connected component labeling.

Figure 4:
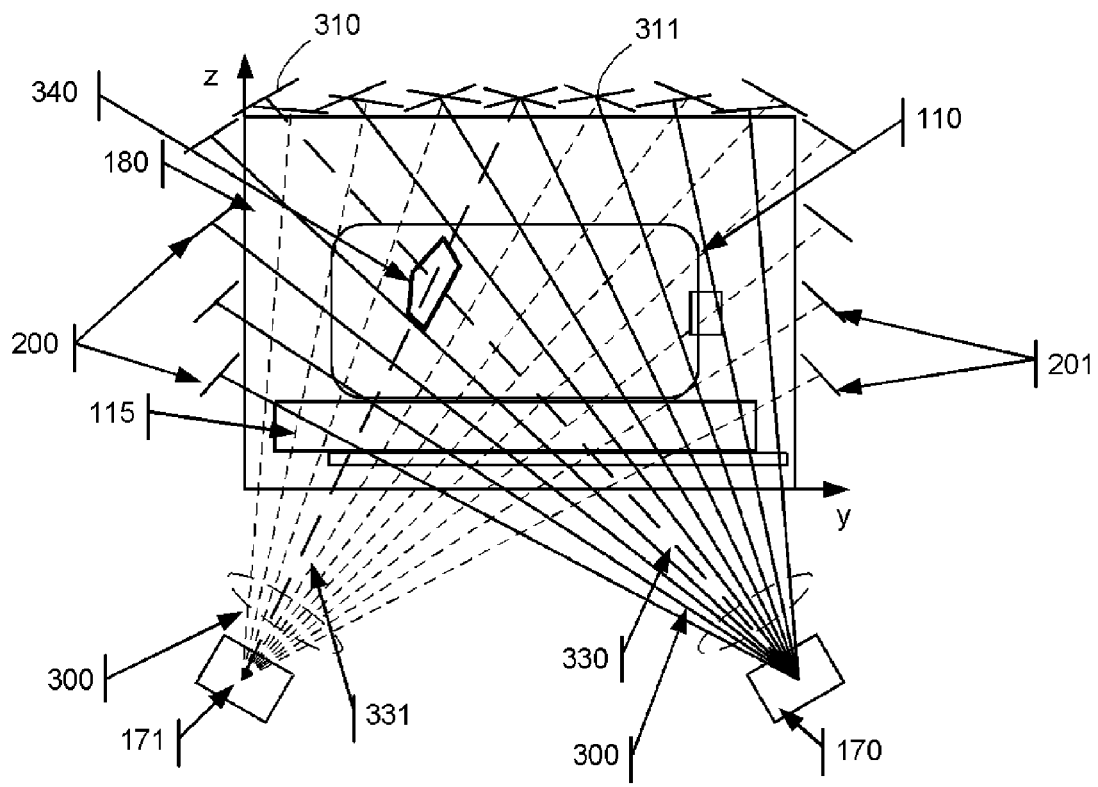
FIG. 4 is a schematic view of one embodiment of the first stage of the X-ray scanning system for identifying a target region.

Referring to FIG. 4, a container 110 is moved on a conveyor 115 through a tunnel 180 in x-direction, perpendicular to the plane of the Figure. A first X-ray generator 170, C1, with an X-ray emitting focus projects a fan of X-rays 300 through a slit collimator onto an array of detectors mounted on printed circuit boards 200. One of ordinary skill in the art would appreciate that only a small sampling of detectors are shown in FIG. 4 and that a typical system would have a far greater number of detectors, preferably 700 to 800, more preferably 740. As shown, the orientation of the fan plane is perpendicular to the conveyor surface. While a container is being moved along the conveyor surface, the detectors are read out repeatedly, and their signals are converted into digital format by detector electronics that are also mounted on the detector boards 200. The data are being processed and sorted further and stored in a computer [not shown] for display on a monitor [not shown]. Each horizontal line on the monitor corresponds to one particular detector in the array. Therefore, in a system using 740 detectors, the full image is composed of 740 lines.

A second X-ray camera, C2, consisting of X-ray generator 171, slit collimator (not shown) and detector array 201 is mounted in a different orientation, and offset in conveyor direction, by typically 100 mm. The detectors aligned with this camera are sampled essentially simultaneously with the detectors of the first camera and produce a second image displayed on a monitor.

Operationally, an item 340 located within the container 110 is recognized in the course of the first stage scan using a detection algorithm or by operator analysis, depending upon the system mode chosen. With the item 340 identified, the approximate centerline X-ray projections 330, 331 that pass through the object can be determined. Each of the centerlines 330, 331 is associated with a certain detector channel, 310 and 311 respectively in each view.

Figure 4A:
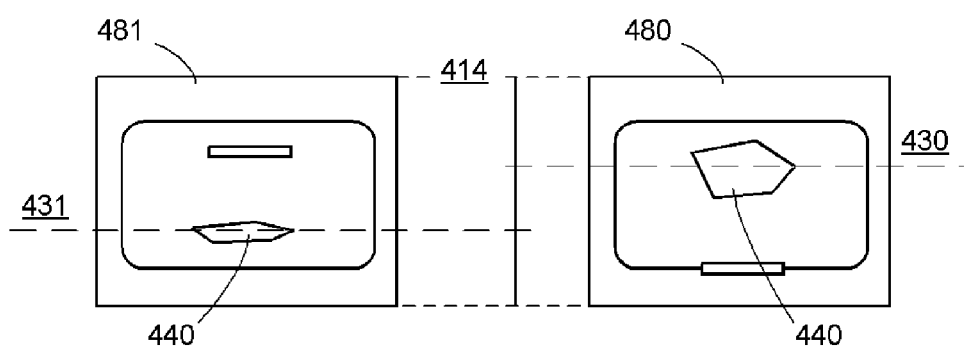
FIG. 4a depicts exemplary images for identifying the location of an item within a container.

Referring to FIG. 4a, once the detector channels have been determined, the location of the associated item 440 can be found in the y-z coordinate system. Two images 480, 481 corresponding to the two views are shown. With knowledge of the detectors associated with the centerlines 431, 430 and the range of detectors defined, the y and z coordinates of the item 440 can be derived. The x-coordinate is defined by the direction of conveyor motion and is known because the conveyor motion control system, timing of X-ray exposure, and the fixed offset of the two scan planes are known. The x-coordinate can, for example, be referenced to the beginning, or leading edge of the container, which can be detected by a light curtain or similar position-detecting device. In particular, the two images are referenced to each other precisely in the x-coordinate direction.

The purpose of this triangulation or localization of identified items in a container is to generate control commands that can be used to position and focus the inspection region or inspection volume of the second stage scanning system on the identified item. Therefore, the first inspection stage quickly locates potential threats and determines their coordinates, as referenced to the system, while the second stage focuses on better determining the nature of the identified potential threat. It should be appreciated that, because the first stage characterization of a threat is loosely based on features in X-ray images, it will locate, find, and label, as a potential threat, items which are innocuous, in addition to real threats. Therefore, the performance of a detection system based only on the first stage, as described, suffers from a high false alarm rate.

One of ordinary skill in the art would also appreciate that other elements of the first stage scanning system are not depicted in FIG. 1 but would be included in an implementation of the system. For example, a shielding curtain is positioned at both the entrance and exit of the system to protect against radiation leakage to the surrounding environment. The system is controlled by a data interface system and computer system that is capable of rapid, high data rate processing, is in data communication with storage media for the storage of scan data and retrieval of reference libraries, and outputs to a monitor having a graphics card capable of presenting images.

It should also be appreciated that a second stage scan may not be required. In one embodiment, radiographic images from the first stage scan are displayed on a computer monitor for visual inspection with target regions or potential threats identified. An operator may dismiss some of the identified regions or threats based on context, observation, or other analytical tools. If no threats are identified, the container is cleared to exit the inspection system without subjecting it to the second stage of scanning. However, if the operator is unable to resolve an area as being a non-threat, the area is identified as a target region.

The second stage inspection or scanning system closely inspects the identified target locations by deriving more specific information, or a signature, and confirming the first stage threat alarm only if the obtained signature matches the signature of a threat substance or threat item. An alarm confirmed by the second stage system are then taken seriously by operators and indicate the need for further inspection, including, but not limited to, operator image interpretation, additional scanning, and/or hand searching the container.

In one embodiment, the second stage scanning system uses diffracted or scattered radiation to determine the properties of a material, obtain a signature, and, accordingly, identify a threat. Diffracted or scattered radiation comprises photons that have experienced an interaction with the object under investigation. In the special case of small angle scattering, the majority of interactions are elastic or energy-conserving; specifically, the diffracted photon has the same energy as it had before the interaction, just its direction of propagation has changed. If the energy distribution of the scattered photons is being analyzed by an energy-dispersive detector system, which is commercially available, certain properties of the material causing the scatter are being encoded in the signature. Photons scattered under small angles are scattered selectively due to interference effects. Since the process does not change the energy of the photons the signal also contains the distribution of the primary radiation in a simply multiplicative way. The incoming primary radiation, as well as the scattered radiation, encounter further spectral modifications due to other types of interactions, such as Compton scatter and photoelectric absorption, which are not energy preserving. If one wants to view the characteristics of the scattering material, other distracting spectral effects have to be removed.

The detected signature of a threat is therefore a combination of X-ray properties. One important property is a BRAGG diffraction spectrum, observed at small diffraction angles between 2 and 8 degrees, with a preferred value around 3 degrees.

Figure 5:
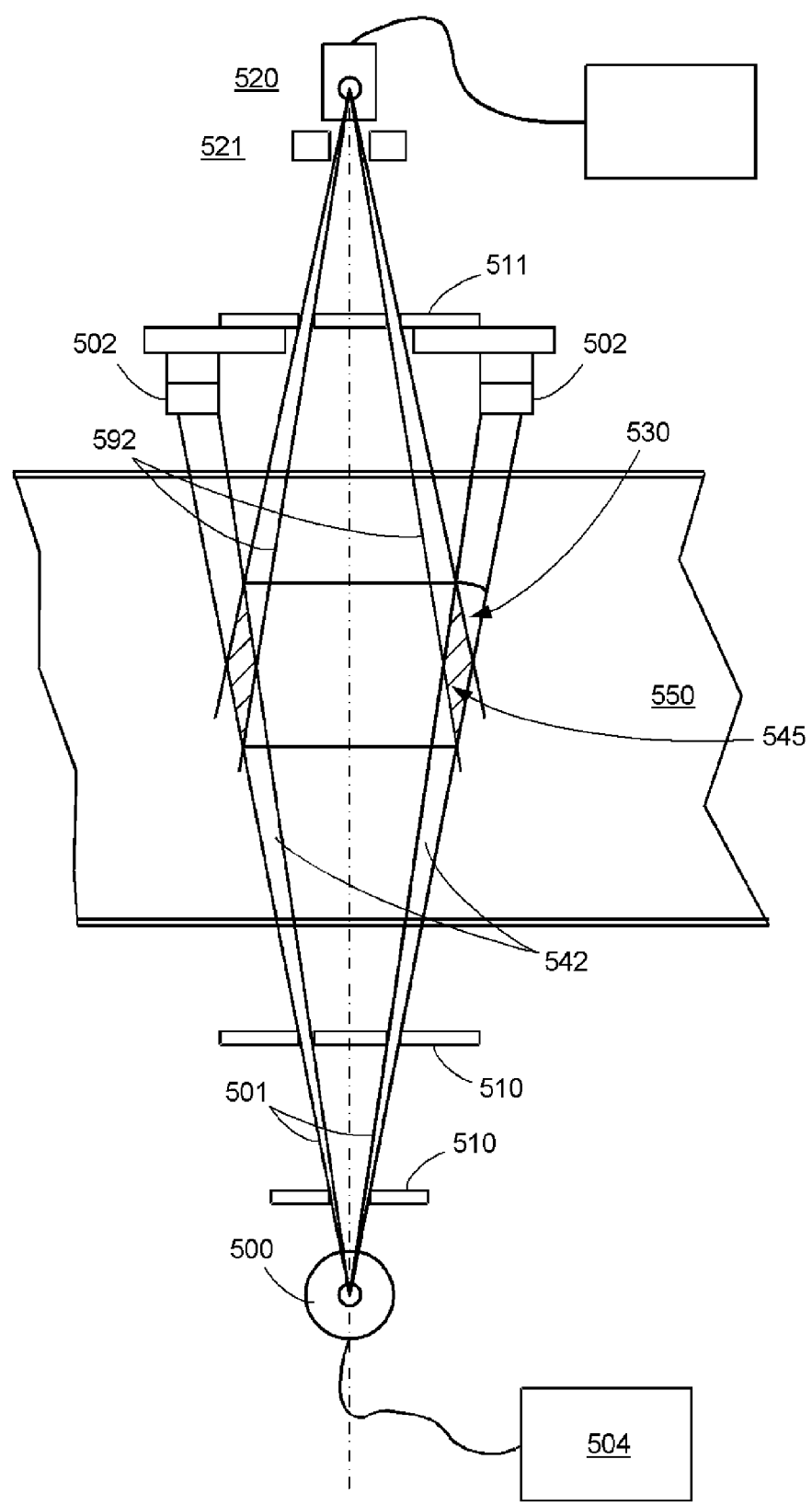
FIG. 5 is a schematic diagram of a cross-section of one embodiment of a beam delivery system for use in a second stage scanning system.

FIG. 5 shows schematically a cross section of a preferred beam delivery system used to obtain BRAGG spectra at small angles. Other beam delivery systems can also be used in the present invention, including those disclosed by Kratky, et al. in Austrian Patent No. 2003753 and Harding in U.S. Pat. No. 5,265,144. The system depicted in FIG. 5 further includes a transmission detector.

A beam delivery system separates the photon radiation emitted by the focus 500 of the X-ray source 504 into a plurality of beams. A beam 501 is formed by passing through apertures 510 and is directly detected by detectors 502, which are within the beam's direct line-of sight. These beams are referred to as transmission beams. Scatter interactions are detected by blocking direct line-of-sight detection through the use of ring apertures 510, 511 and exposing the associated detector 520 only to scattered radiation 592. Therefore, scatter radiation, generated when certain beams interact with an inspection region or volume 545, can be detected in the same apparatus as transmission radiation.

The choice of ring aperture diameters, distance to focus, and distance to detector determines the effective scatter angle 430 of the photons falling on the detector. In one embodiment, the scatter angle 530 is approximately the same for substantially all photons detected by the detector of the scattered radiation. It is preferred to configure the beam delivery system to establish an effective scatter angle of between two and 8 degrees. It is more preferable to have a scatter angle at or about 3 degrees. Using a beam delivery system having a circular symmetry has the advantage of obtaining a scatter contribution from a larger volume of the material being inspected, thereby increasing the inherently weak scatter signal. Additionally, the scatter spectrum can be cost efficiently detected using only a single detector channel 520 with an entrance aperture in the shape of a hole 521.

The scatter signal is generated by positioning the target region 545, identified in the first stage scan, between the beam forming apertures, irradiating that region 545 using the conical beam 542, and making sure scatter radiation from the target region 545 can be detected by the scatter detector. The target region 545, often contained within a container 550, is in the shape of a tube or ring 545 and is referred to as the inspection volume or inspection region. The length, diameter, and wall thickness of the inspection volume depends on the particular shape of the elements of the beam delivery system, including focus size, ring aperture diameter and width, detector opening and overall distance. In a preferred embodiment for the inspection of large luggage, the inspection volume is at or about 60 cubic centimeters.

Figure 6:
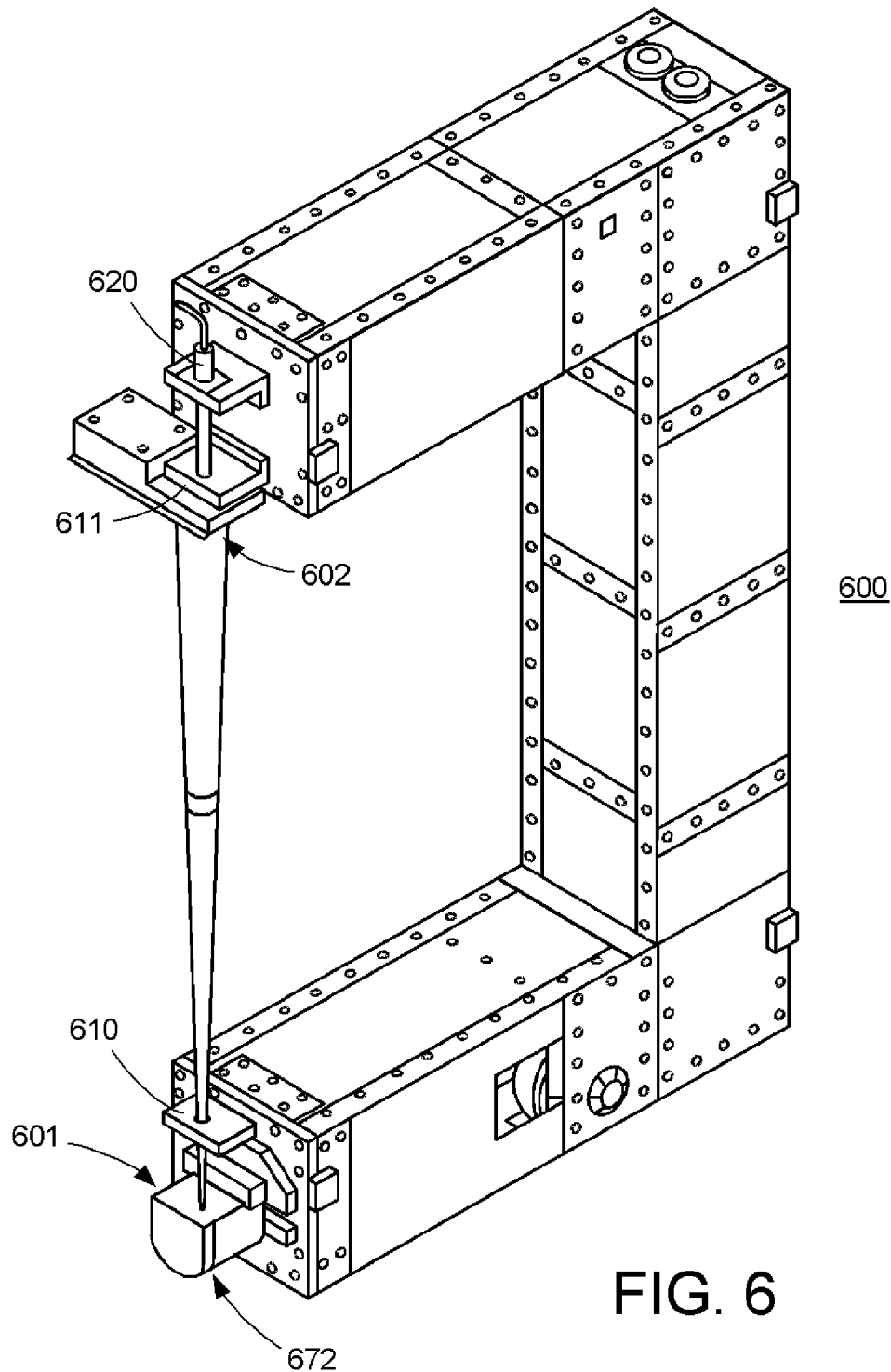
FIG. 6 is a schematic diagram of one embodiment of the beam delivery system of the second stage scanning system.

In one embodiment, as shown in FIG. 6, the components of the beam delivery system are mounted to the open ends of a rigid support structure 600 formed in the shape of a C (referred to herein as a C-arm) and aligned with a tolerance of at or about 0.1 millimeters. A first arm of the C-arm comprises a X-ray tube with X-ray focus 672, a beam limiting aperture hole mounted to the tube head 601, and a ring-shaped aperture 610. A second arm holds comprises a transmission detector array 602, a second ring aperture 611, and an energy dispersive detector 620, equipped with an aperture hole.

The energy dispersive detector 620 is positioned to receive scattered radiation from a target object placed on the conveyor running between the arms of the C-arm support structure where a first arm is above the conveyor and a second arm is below the conveyor. The transmission detector is positioned to receive radiation attenuated by the same target object. It is preferable for the C-arm to be mobile and capable of moving in the x-direction along the length of the conveyor. Therefore, the C-arm with tube and detectors can be re-positioned along the length of the conveyor.

In a preferred embodiment, the scatter detector 620 is comprised of cadmium telluride or cadmium zinc telluride and is operated at room temperature, or approximate to room temperature, An exemplary embodiment is available from the e-V Products Company, Saxonburg, Pa. This type of detector has a spectral resolution performance that is well matched to the limited angular requirements of this application, and therefore the limited spectral resolution of the beam delivery system.

In one mode of operation, the potential threat locations inside a container are found automatically by the first stage, and, based upon the physical coordinates obtained through triangulation, the second stage scanning system is automatically positioned to generate an inspection region that substantially overlaps with the identified target region. Where multiple threat locations are identified, the second stage scanning system is sequentially repositioned to focus on each subsequent target region. To scan each target region, the second stage X-ray source is activated and the scatter detector and transmission detector are sampled simultaneously. In a preferred embodiment, a transmission spectrum associated with the detected transmission data is characterized using a look up reference, figure, table, or chart, and the scatter spectrum is normalized using that identified transmission spectrum.

In another mode of operation, an operator actively identifies images that he or she believes corresponds to a potential threat. X-ray images from the first inspection stage are displayed to the operator, and the operator points to a suspicious object as it appears in both views. To support this functionality, operators use a computer system, comprising a mouse and monitor, to position cross hairs over the areas of interest on each of the images. Using coordinate data generated through triangulation, the second stage scanning system automatically positions itself such that an inspection region overlaps with the target region, activates the X-ray source and simultaneously samples the scatter detector and transmission detector. In a preferred embodiment, a transmission spectrum associated with the detected transmission data is characterized using a look up reference, figure, table, or chart, and the scatter spectrum is normalized using that identified transmission spectrum.

As discussed above, a transmission detector is integrally formed with the beam delivery system, as shown in FIGS. 5 and 6. A preferred transmission detector comprises a 16 channel array of dual energy detectors. The detector array further comprises pairs of detectors, including a low energy channel that receives and measures a first amount of radiation first (low energy) and a high energy channel that receives and measures a substantial portion of the balance of radiation (high energy). Dual energy detection has been described in connection with the linear scan arrays of the first inspection stage and is known to persons of ordinary skill in the art.

Figure 7:
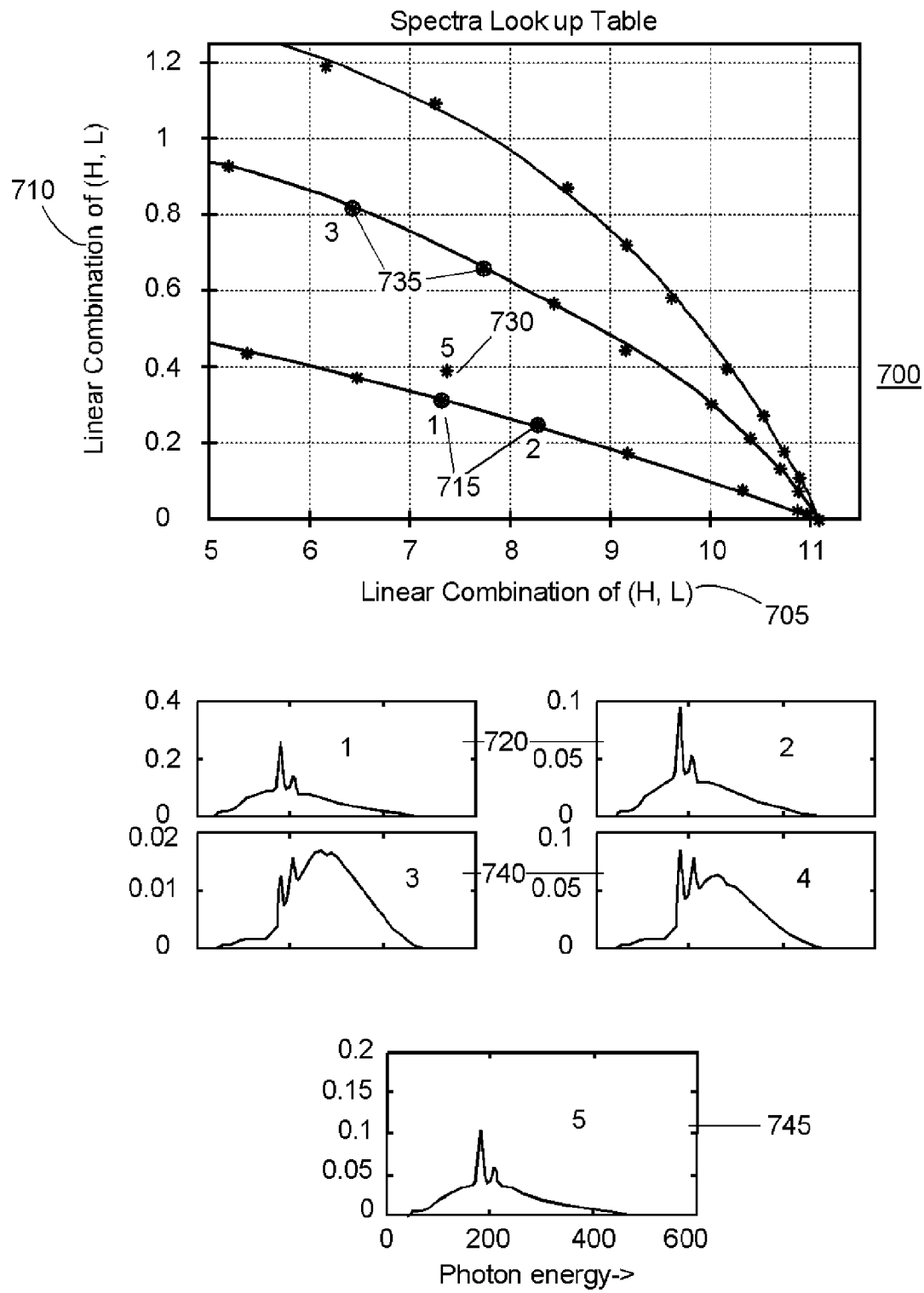
FIG. 7 is an exemplary look up source for transmission spectra.

The low energy and high energy detectors measure a plurality of low energy and high energy values that can be used to characterize the material being scanned. In a preferred embodiment, low energy and high energy data are used to reference a look up reference, figure, table, or chart (referred to as a look up source) which contains transmission spectra arranged in accordance with corresponding high and low energy values. The look up source is constructed with high energy values on one axis (i.e. the x-axis), and low energy values on a second axis (i.e. the y-axis). Referring to FIG. 7, an exemplary look up source 700 is shown. The source 700 is a graph with high energy values on the x-axis 705 and low energy values on the y-axis 710. Points 715 corresponding to measured spectra 720 are positioned on the graph according to certain linear combinations of the measured high and low dual energy detector signals on the x and y axis.

The transmission spectra used to normalize scatter data is therefore identified by obtaining high energy and low energy data values, identifying the point on the graph corresponding to the detected high and low energy values, and looking up the spectrum associated with that point. Where the detected high and low energy values yield a point on a graph that corresponds to an intermediate point 730 proximate to pre-established points 735, 715, a corresponding transmission spectra 745 can be calculated by performing a two-dimensional interpolation of the spectra 740, 720 associated with the pre-established points 735, 715.

To create the look up source, an exemplary approach places various materials of known composition and thickness, exposes them to X-ray sources, measures the resulting high and low energy data values, and uses the scatter detector to measure the corresponding transmission spectrum. More specifically, the beam path of the beam delivery system is modified to allow a direct beam from the focus through the pinhole to fall on the energy dispersive scatter detector. To further reduce the photon flux into a range that can be tolerated for energy-dispersive measurement, the current of the X-ray source is preferably reduced by a large factor, e.g. 100. Under these parameters, the scatter detector can be used to measure the transmission spectrum. Materials of known composition and thickness are placed in the beam path. The materials are exposed to X-ray radiation. Dual energy measurements are made using the dual energy detectors and a transmission spectrum is obtained using the scatter detector. Through this approach, for each material composition and thickness, a transmission spectrum is obtained and correlated with discrete pairs of dual energy transmission detector readings. This information is then arranged on a chart with the high energy value of the dual energy detector measurement on the x-axis, and the low energy value on the y-axis.

It should be appreciated that, in the disclosed embodiment, the spectra are the looked-up objects of the look up source.

Instead of the spectra, however, the look up source can alternatively consist of spectral attenuation functions related to the attenuation of the materials placed in the beam when the look up source is being generated. The spectrum can then be obtained by multiplying one fixed spectrum, for example the spectrum measured without the material placed into the beam, with the spectral attenuation function retrieved from the look up source. Alternatively, the look-up source can contain numbers that are the parameters of analytical expressions, e.g. polynomials, which are formed to describe the attenuation functions in a parametric way.

The presently described approach is preferred because it enables the construction of a transmission detector array from lower cost materials, as opposed to constructing the array using more expensive energy dispersive detectors and support electronics. Moreover, it also addresses the difficult problem of using energy dispersive detectors to measure transmission spectra at the high flux rates that are experienced at the location of the transmission detector in the given configuration and at the same time at which the scatter data are recorded. The required strong attenuation of the transmission beams is a difficult problem that is avoided using the present invention. The look up table is an important element because the preferred dual energy detectors used in the transmission detector cannot deliver spectra directly.

Transmission spectra are being used to correct the scatter spectra that are being recorded by the energy dispersive detector. Normalizing scatter spectra with transmission spectra corrects for the confounding effects introduced by the specific spectral distribution of the primary radiation, as emitted from the X-ray source, as well as by spectrum-distorting effects known as beam hardening. To correct the scatter spectra, the detected scatter spectra are divided by the looked-up transmission spectra.

A normalized scatter spectrum exhibits a plurality of features. A first feature is that the location of the peaks and valleys of the spectrum are determined by the molecular structure of the materials located in the probe region. A second unrelated feature is that the average spectral signal of the normalized scatter signal, which can be of varying intensity, is linearly related to the gravimetric density of the material in the probe region. This can be used for threat discrimination since most explosives, particularly military explosives, have a density range above that of most other plastic or food items in suitcases.

In one embodiment, the normalized scatter signal is used to identify a threat item by comparing the obtained normalized scatter spectrum and/or spectral signal with a library of scatter signals from known threat items. This comparison can occur automatically by using a processor to compare a library of threat items, stored in a memory, with the obtained scatter signals. Such a library is developed by measuring the normalized scatter signatures of known threat items. In addition to using the transmission detector to generate data used to identify reference spectra, the transmission detector can function in a plurality of other ways. In one embodiment, the transmission detector acts as a position sensor. The transmission beam is interrupted or attenuated momentarily when an object on the conveyor crosses it. Tracking the moment of interruption can provide information on the physical position of the container on the conveyor and be used to appropriately position the beam delivery system or container.

In a second embodiment, the transmission detector array functions as an imaging detector to provide precise attenuation data for certain areas in containers, like container wall areas, where contraband can be hidden. When the circular beam is centered on an edge of a container, the edge of the container can be imaged in good detail, and can help analyze the edges for concealed threats.

In a third embodiment, transmission detector measurements can be used to determine whether the inspection region is, in fact, the same target region previously identified in the first stage scan. If the transmission data correlates with X-ray characteristics different than those obtained in the first stage scan, the relative positioning of the second stage scanning system and the object under inspection may be modified until the transmission data correlates with the same material characteristics that was identified in the first stage scan.

In a fourth embodiment, transmission detector data are also being used to simplify the algorithm-training procedure of the system, as described below, in particular the collection of threat material properties with irregularly shaped threat samples, like sticks of dynamite.

It should be noted that it would appear because the scatter radiation path and transmission path differ downstream from the scatter volume, there would be inconsistencies in the data when scatter and transmission data are combined. This inconsistency is one example of a number of partial volume effects, solutions for which are addressed herein. However, the inconsistencies are not significant and can be tolerated without encountering significant performance degradation of the system as a whole. As shown, FIG. 5 is not an isometric schematic and, in reality, the scatter angle is preferably about 3 degrees, and the real path differences are comparatively smaller.

As previously discussed, the second stage scanning system positions an inspection region to physically coincide with the target region identified in the first stage scan. The positioning means may be achieved using any method known in the art. In one embodiment, a plurality of control commands is produced in response to the determination of the location of the target region. The control commands are generated by at least one processor in data communication with a plurality of processors capable of executing the aforementioned triangulation techniques and/or determining the intersection of projection lines to identify the location of the target region in three dimensional system coordinates.

The control commands comprise data signals that drive a three-axis control system. The vertical position of the second-stage inspection volume can be adjusted to the target volume or region of the first stage scan by moving the conveyor system up or down. In another embodiment, the control commands comprise data signals that drive the adjustment of the beam delivery system in the second stage scanning system. The beam delivery system adjustment can include any type of adjustment to the collimation or beam focus, including the physical movement of a plurality of apertures horizontally, vertically, or diagonally, the physical modification of the diameter of the ring aperture by, for example, increasing or decreasing the aperture size. In another embodiment, the position of the support structure, or C-arm, can be modified along the conveyor direction to appropriately position the beam delivery system.

The second stage scan may be compromised when the volume of the target region is smaller than the inspection region of the second stage. In such cases, extraneous material, other than the material identified as being a potential threat, such as air, metal, or container edges, may be included. The resulting scatter radiation is therefore a function of multiple material types and may not be readily identifiable as being the signature of a single substance.

In one embodiment, the present invention comprises a threat recognition process that incorporates a training methodology which relies on libraries in which threat signatures are obtained by combining the threat with other common materials, such as clothing, plastic, air, and metals. Specifically, the data used in training and developing the detection process are chosen to include data, which are corrupted by errors based on partial volume data from statistically varying containers and threat and non-threat material combinations. When the inspection volume is partially filled with a threat substance and partially filled with a second innocuous substance, a combination signal will be detected by the second scanning stage. The automatic threat recognition methodology recognizes the threat from the combination signal based upon the aforementioned training. An exemplary automatic threat recognition methodology, based on neural networks, is described in U.S. patent application Ser. No. 10/910,250 and is incorporated herein by reference.

In a second embodiment, the detected scatter data is corrected for the effects of extraneous materials by pre-processing the data. The motion control system tracks where the inspection volume or region is located in relative to a specific reference point, such as the approximate outlines of the container, and relative to the conveyor system. Because of the ability to measure and track these reference points, the amount and portion of the inspection volume occupied by the conveyor structure can be determined. The conveyor structure includes the belt material as well as the structural member that is underneath the conveyor, which is referred to as the slider bed.

To correct the scatter spectrum for the presence of the conveyor in the inspection volume, the scatter spectrum of the conveyor materials is measured and stored in a reference database. When the scatter spectrum of the inspection region is detected and it is determined that the conveyor occupied a portion of the inspection region, the scatter spectrum is corrected by multiplying the conveyor material scatter spectrum by a weighting factor to account for the size of the inspection volume occupied and that amount is subtracted from the measurement.

Similarly, when part of the inspection volume is filled with air, as in cases when suitcase walls are targeted by the inspection volume, it is known that the contribution of the air-filled portion of the inspection volume to the scatter signal is approximately zero, and therefore, substantially all of the scatter signal can be attributed to the material in the remainder of the inspection volume. By accounting for the air volume contribution, the characterization of the material in the remaining inspection volume is rendered more precise. Optical detectors, such as a plurality of light-curtains, can be positioned across and within the scanning system to generate control signals that convey information about the height and edges of the container relative to the conveyor system and relative to the inspection region. It therefore can be calculated which portion of the inspection region is filled with air.

In another embodiment, transmission values for the scatter beam are measured by an array detector. An exemplary array comprises 16 channels and yields transmission data for 16 subdivisions within the inspection volume. The transmission values can be used to characterize the material distribution in the inspection volume. Based on these transmission values, approximate mass values can be determined for masses contained in each of the 16 subdivisions. For example, where the transmission detector value returns a value indicating the subdivision has material with zero thickness, it can be assumed that the subdivision is occupied by air.

In one embodiment, the inspection volume is subdivided. By reducing the size of the inspection region, one can ensure that fewer differing materials occupy the same region and can therefore avoid the complex composite signals that get generated when multiple materials fill a single inspection region. In one embodiment, system resolution is increased by providing multiple energy dispersive detectors, such as 2, 3, 4, 5, 6 or more, in place of a single energy dispersive detector as shown in FIG. 4.

Figure 8:
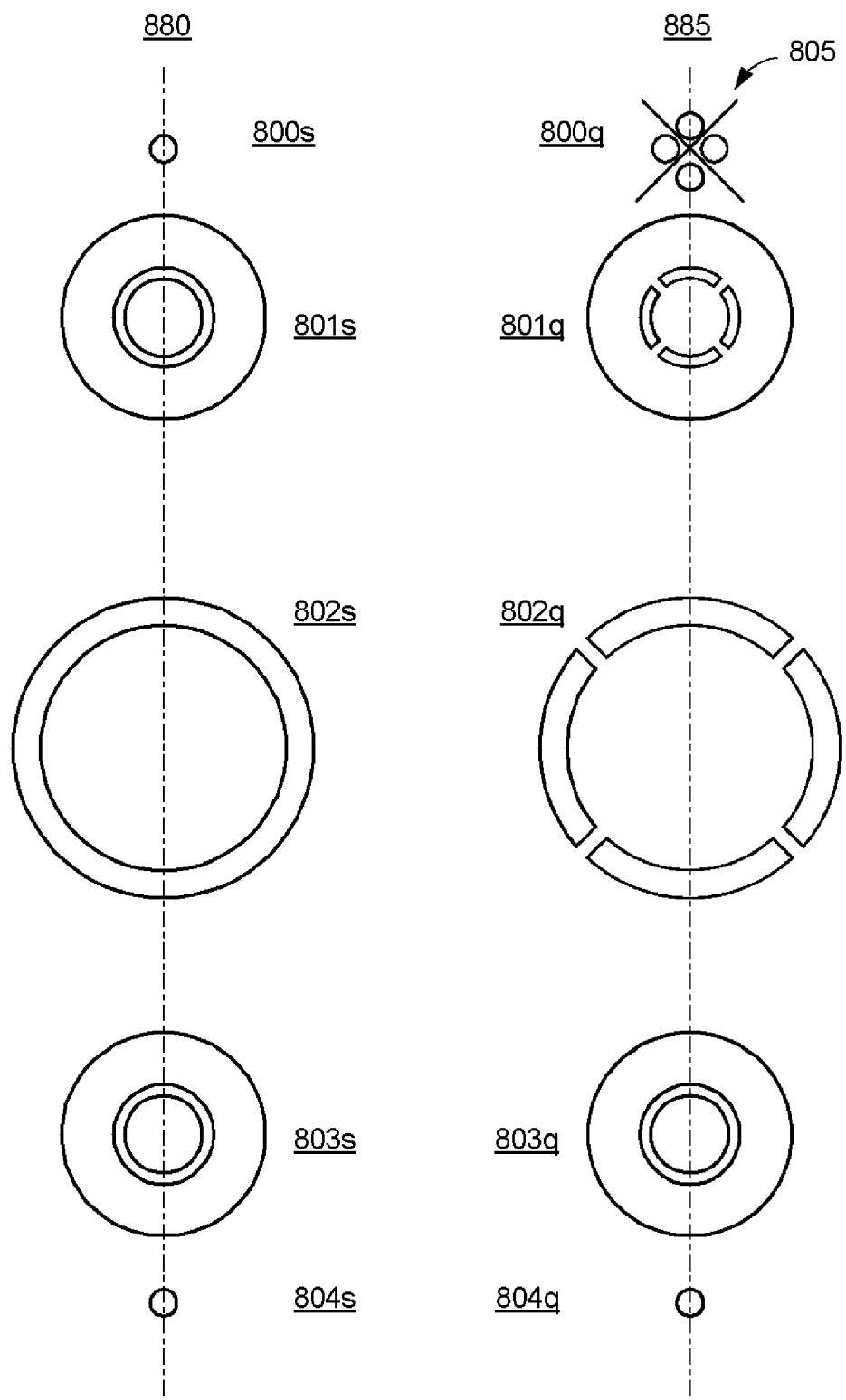
FIG. 8 is a schematic representation of a beam delivery system having multiple energy dispersive detectors.

Referring to FIG. 8, a schematic representation of the beam delivery system of FIG. 5 880 is shown relative to a beam delivery system having multiple energy dispersive detectors 885. A first system 880 comprises single detector 800$s$, circular aperture 801$s$, inspection volume 802$s$, circular aperture 803$s$, and X-ray focus 804$s$. The dark areas represent the presence of radiation blocking material, e.g. ¼ inch lead alloy, and the white areas represent areas that are transparent to X-rays above 30 keV. A second system 885 comprises an X-ray focus 804$q$, circular aperture 803$q$, divided inspection volume 802$q$, detector side beam shaping aperture 801$q$, and quadruple detector 800$q$. The aperture 801$q$ is center-symmetric and consists of four slits, each conforming to part of a circle. The centers of the circular slits are chosen to be of the same pattern as the detectors of the quadruple detector 800$q$. For example, if the detector cluster consists of four channels centered on the four corners of a 2 by 2 mm square, the centers of the partial and circular apertures lay on a circle with diameter equal to the square root of 2 times 2 mm. The resulting inspection region for each individual detection region is about one quarter of the full inspection volume. A subdivided inspection region provides a higher spatial resolution of the second stage inspection. Clusters of energy dispersive detectors with their supporting electronics are commercially available from companies such as eV Products, Saxonburg, Pa.

If more than one scatter detector is being employed, a collimating system of vanes can be placed in front of the detector cluster orthogonal to the surface of the detector and in line with the plane of separation between each detector. Using a separator 805, diffracted radiation is more effectively limited to reach the appropriate channel in the cluster and, consequently, detected signals are more readily associated with materials from specific areas within the inspection region. The separator 805 extends from the surface of the detector cluster toward the surface of the adjacent aperture. The number of separator vanes is dependent on the number of detectors. A typical vane material and thickness is lead alloy of 0.5 mm thickness.

Figure 9:
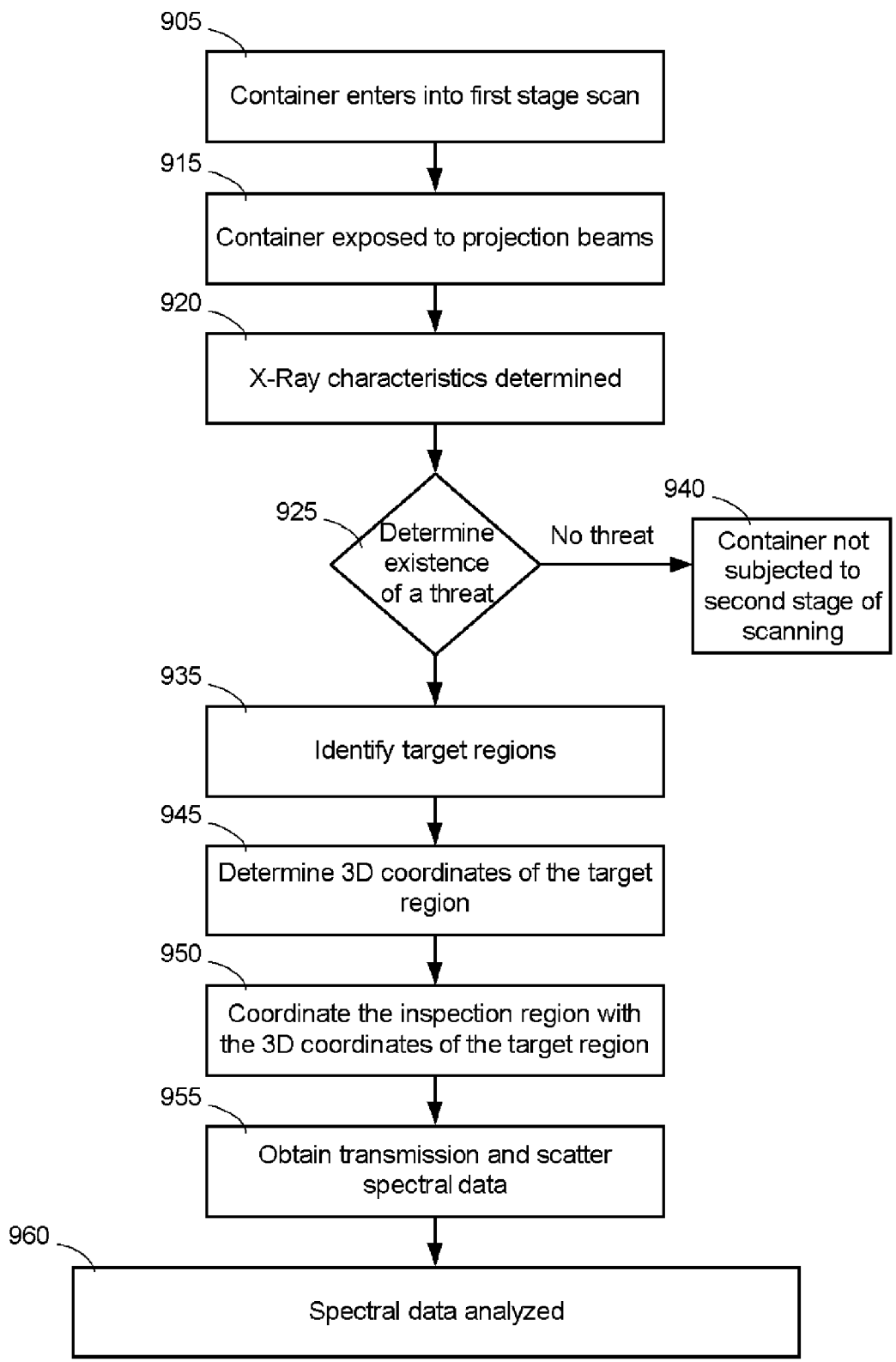
FIG. 9 is a flow diagram depicting one method of practicing the present invention.
Figure 10:
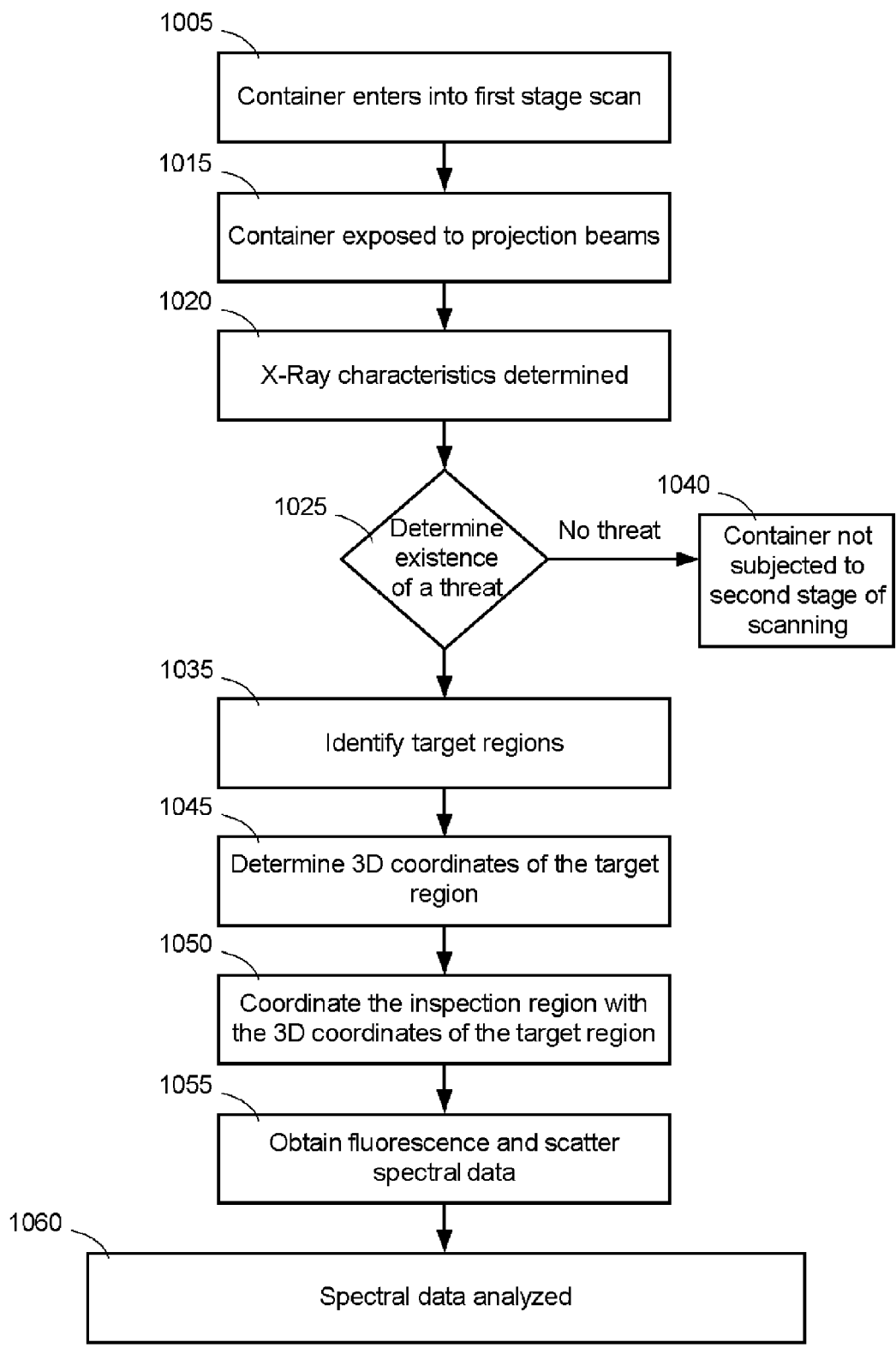
FIG. 10 is a flow diagram depicting one method of practicing the present invention.

Referring to FIG. 9, a flowchart summarizing the operational process of one embodiment of the present invention is provided. A container enters into the first stage scan 905 where it is exposed to a plurality of projected beams 915. From that exposure, X-ray characteristics are determined 920 and target regions containing potential threats are identified 925, 935. If no potential threats are identified, the container is not subjected to a second scanning stage 940. The three dimensional coordinates of the target region is determined 945 and, accordingly, the inspection region generated by the second stage scanning system is coordinated to coincide with the target region 950. The inspection region is subjected to X-ray radiation in order to obtain transmission and spectral data 955. The spectral data is then analyzed 960 to determine the existence of a threat. The data collected in the second stage scan comprises both localized dual energy transmission data and localized BRAGG diffraction spectra, which are subject to statistical variances, originating from photon signal fluctuations, partial volume limitations, or variations of the type of luggage and their contents, among other causes. As such, it is preferred to have a processing methodology that accounts for the fact that the raw data is not sufficiently sensitive to detect threats with sufficiently low false alarm rate.

Alternative First Stage Scanning System

Referring back to FIG. 1, a dual stage scanning system 100 comprises conveyor systems 121, 122 for moving containers, baggage, luggage, or similar object 105 through a plurality of scanning stages 110, 115. In this alternative embodiment, dual stage X-ray scanning system 100 comprises a Computed Tomography (CT) Unit as a first stage 110 and a Substance-Identification Unit (S-I Unit) as a second stage 115. In an exemplary embodiment object 105 is, but is not limited to, a piece of baggage and will be described as such hereinafter. Baggage 105 moves through the two stages via conveyor systems 121, 122 in the direction of arrow 125 (along the X-axis). Conveyor systems 121, 122 are controlled and coordinated by Luggage Transport Sub-systems (LTS) 141, 142, respectively, thus operating the combined system 100 at a high-duty cycle. Both the first stage and second stage further comprise computer processing systems 131 and 132, for respectively receiving and processing, CT (Computed Tomography) data signals and small angle X-ray diffraction spectra of a threat location. Optionally, a bypass conveyor belt is provided between the first stage 110 and second stage scanning units 115 that enables the object 105 to be passed through the scanning system without having to be first inspected by the second stage scanning unit 115. Such a bypass can be used if the first stage scanning unit 110 indicates that no threat exists, or no suspicious region exists, in the object 105 based on the first stage scan.

In one embodiment, first stage 110 is a CT unit, generating three dimensional (3D) imaging data, coded in gravimetric density. Computer processing system 131 of the first stage 1110 generates automatic image analysis resulting in, but not limited to, the approximate shape, size, density, weight and, location of potential threats. As the piece of baggage 105 is transported into second stage 115 via conveyor system 122 along arrow 1125, the computer processing system 132 of the S-I Unit receives a three dimensional coordinate map of the threats. Processing system 132 also receives the image volume file from the CT Unit via suitable transmission links, such as, but not limited to an Ethernet LAN (Local Area Network) connection.

The S-I Unit subsequently interprets the three dimensional coordinate map of threats and image volume data in second stage 115 and reacts by moving its probing beams into the position best suited for sampling the threat resolution information. In second stage 115, based upon its automatic threat resolution algorithm, the S-I Unit provides data to an operator who can manually activate an alarm or clear an object, or, based on the data, the system can automatically clear the objector activate an alarm.

Figure 12:
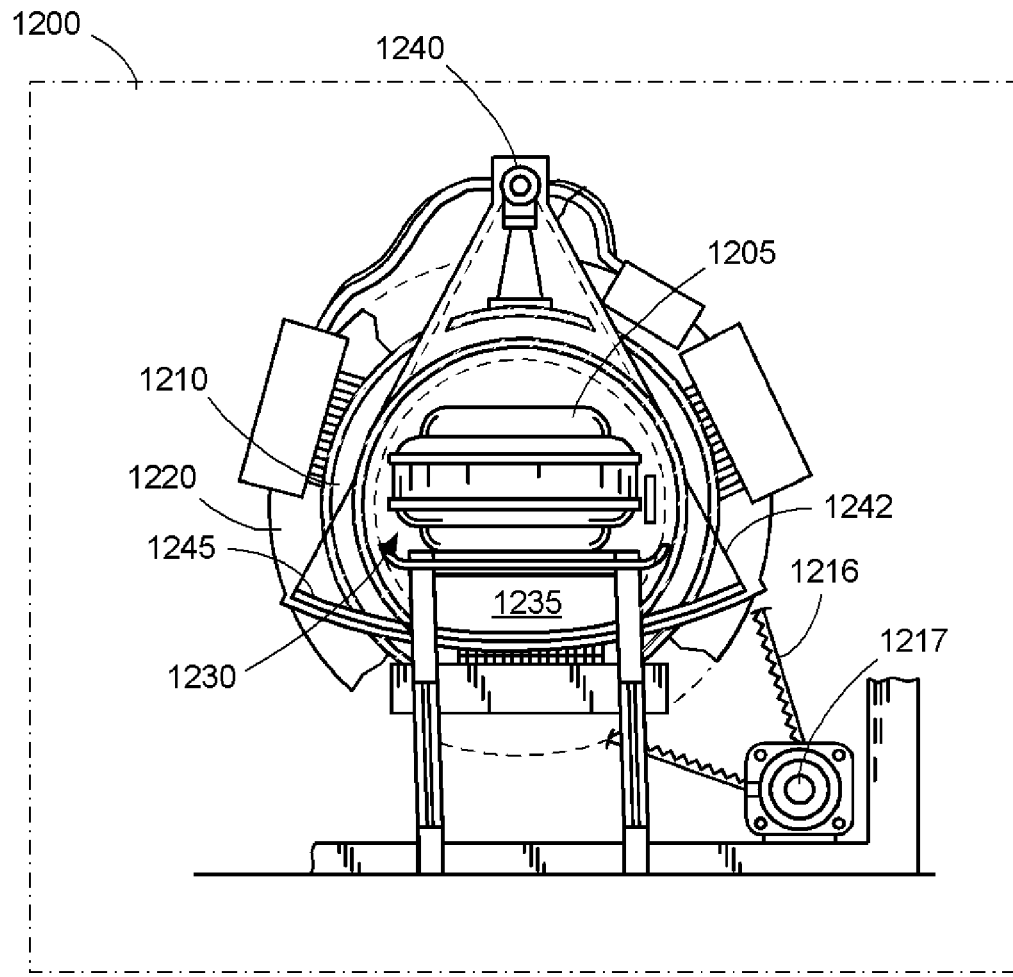
FIG. 12 is a schematic diagram of one embodiment of a first stage CT scanning system.

As mentioned above, first stage 1110 of the CT Unit of the present invention is preferably a conventional CT-scan system as is well known to those of ordinary skill in the art. FIG. 12 is a depiction of a perspective tunnel view along the conveyor system of one embodiment of the present invention, and in particular, shows the functional components of CT Unit 1200 as employed in an exemplary embodiment of first stage 1110. CT Unit 1200 comprises an annular shaped rotating platform or disk 1210 disposed within a gantry support 1220 for rotation about a rotation axis that is preferably parallel to the conveyor and direction of travel of baggage 1205. Rotating platform or disk 1210 is driven about the rotation axis by any suitable drive mechanism, such as a combination of belt 1216 and motor drive system 1217, or any other suitable drive mechanism as is well-known in the art. Rotating platform 1210 defines a central aperture 1230 through which conveyor system 1235 transports baggage 1205. CT system 1200 further includes an X-ray tube 1240 and a detector array 1245 which are located on opposite sides of platform 1210.

As described earlier with reference to FIG. 1, CT Unit 1200 also comprises a computer processing system (not shown in FIG. 12) for receiving and processing CT data signals generated by the detector array, and for generating the necessary command signals for operating and controlling the Luggage Transport Sub-Systems (LTS) 141, 112. The computer system preferably also includes a monitor (not shown) for displaying information including generated CT images.

In one embodiment, X-ray tube 1240 is controlled by a dual-energy X-ray tube control system known to those of ordinary skill in the art. Dual energy X-ray techniques for energy-selective reconstruction of X-ray CT images are particularly useful in indicating a material's atomic number in addition to indicating the material's density, although it is not intended that the present invention be limited to this type of control system. While the present invention describes the details in connection with single-energy data, it should be understood that the description is applicable to multiple-energy techniques as well.

In one embodiment, X-ray tube 1240 generates a preferably conical beam 1242 of X-rays that pass through a three-dimensional imaging field, through which baggage 1205 is transported by the conveying system 1235. After the conical X-ray beam 1242 passes through baggage 1205 transported through the imaging field, it is received by detector array 1245, which in turn generates signals representative of the densities of exposed portions of baggage 1205. Conical beam 1242 thus defines the scanning volume or imaging field. Platform 1210 rotates about its rotation axis, thereby moving X-ray source 1240 and detector array 1245 in circular trajectories around baggage 1205 as it is continuously transported through central aperture 1230 via conveyor system 1235, thus generating a plurality of projections at a corresponding plurality of projection angles.

Information from the detector array 1245 is subsequently sent to the processing system to determine the attenuation of the X-rays as they pass through baggage 1205. Using Conventional Tomography and three dimensional image construction methods, known to persons of ordinary skill in the art, the attenuation information is used by the processor to compute a density for each voxel in a three-dimensional image of the bag 1205.

Voxels in a specified density range, which are physically adjacent in three dimensions and have a density variation less than a predetermined threshold are grouped and assigned with a label for identification. Because this adjacency check is performed in three dimensions, thin regions of any shape in any orientation are readily identified. Further, the number of voxels in each region is determined and compared to a threshold. In an exemplary method of the preferred invention, small regions are rejected as harmless; small regions are defined as those regions containing only a small number of voxels or a number of voxels below a certain threshold. Large contiguous regions, that is, regions containing more voxels than a preset threshold, are identified as suspect. The mass contained in any suspect region(s) is then calculated by multiplying the volume of each voxel in the region by its density. If the resulting mass is greater than a preset threshold, for example, 1000 grams, the region is tentatively identified as a threat region.

Additionally, by taking projections from at least two different angles, it is possible to triangulate the location of the potential threat relative to the physical coordinates of the system. The triangulation process localizes items and/or areas that generate features of interest in the images and identifies their location in the form of system coordinates.

As is well known to those of ordinary skill in the art, thresholds are determined based on an extensive analysis of CT data, such as actual three dimensional CT density data, for many actual threat and non-threat objects. Exemplary thresholds include, but are not limited to, density thresholds, mass thresholds, density-dependent mass thresholds, and process parameters used to carry out a tentative identification of a threat region. Any of such thresholds can be used as a basis to determine whether detected characteristics of materials does, or does not, activate an alarm and/or warrant additional screening via a second stage scan. The extensive analysis includes statistical analysis of the data employing statistical methods such as simulated annealing and genetic algorithms known in the art. This analysis allows for threshold and/or parameter selection based on a particular objective to be met, e.g., false alarm and/or detection rate setting/optimization, discrimination of threat type, and other mechanisms.

The three dimensional image of baggage 1205 under inspection is subsequently presented to an operator for inspection over a suitable video device such as a monitor of the processing system. The threat regions tentatively identified at the first stage are preferably marked and/or tagged for resolution by an operator. If the operator determines that the threat(s) identified are innocuous she may dismiss the threat(s) and clear the baggage without the need for further inspection. In such cases, the baggage or object under inspection may be permitted to continue via a bypass conveyor to the secured area, without having to first pass through the second stage scan. However, if the operator is not able to resolve a threat, subsequent verification of the threat region is then performed by the second stage. Alternatively, the system can be programmed to automatically require second stage scanning if measurements of a region are determined to meet a first pre-defined plurality of values. Further alternatively, the system can be programmed to automatically send the object under inspection via a bypass conveyor to the secured area, without having to first pass through the second stage scan if measurements of a region are determined to meet a second pre-defined plurality of values Referring back to FIG. 11, in order to verify the threat located in first stage 1110 and preferably identify the threat substance, the data required by the S-I Unit in second stage 1115 from the first CT Unit stage 1110 comprise at least a threat map in three dimensions comprising the three dimensional coordinates of the potential threat identified by the CT Unit in first stage 1110 and a three dimensional density distribution of the remainder of baggage 1105. In second stage 1115, computer processing system 1132, via the use of an algorithm subsequently converts the threat map into a sequence of motion control commands, needed to line up the S-I Unit in second stage 1115 inspection regions with the threat locations tagged by the first stage 1110, as further discussed below.

Figure 13:
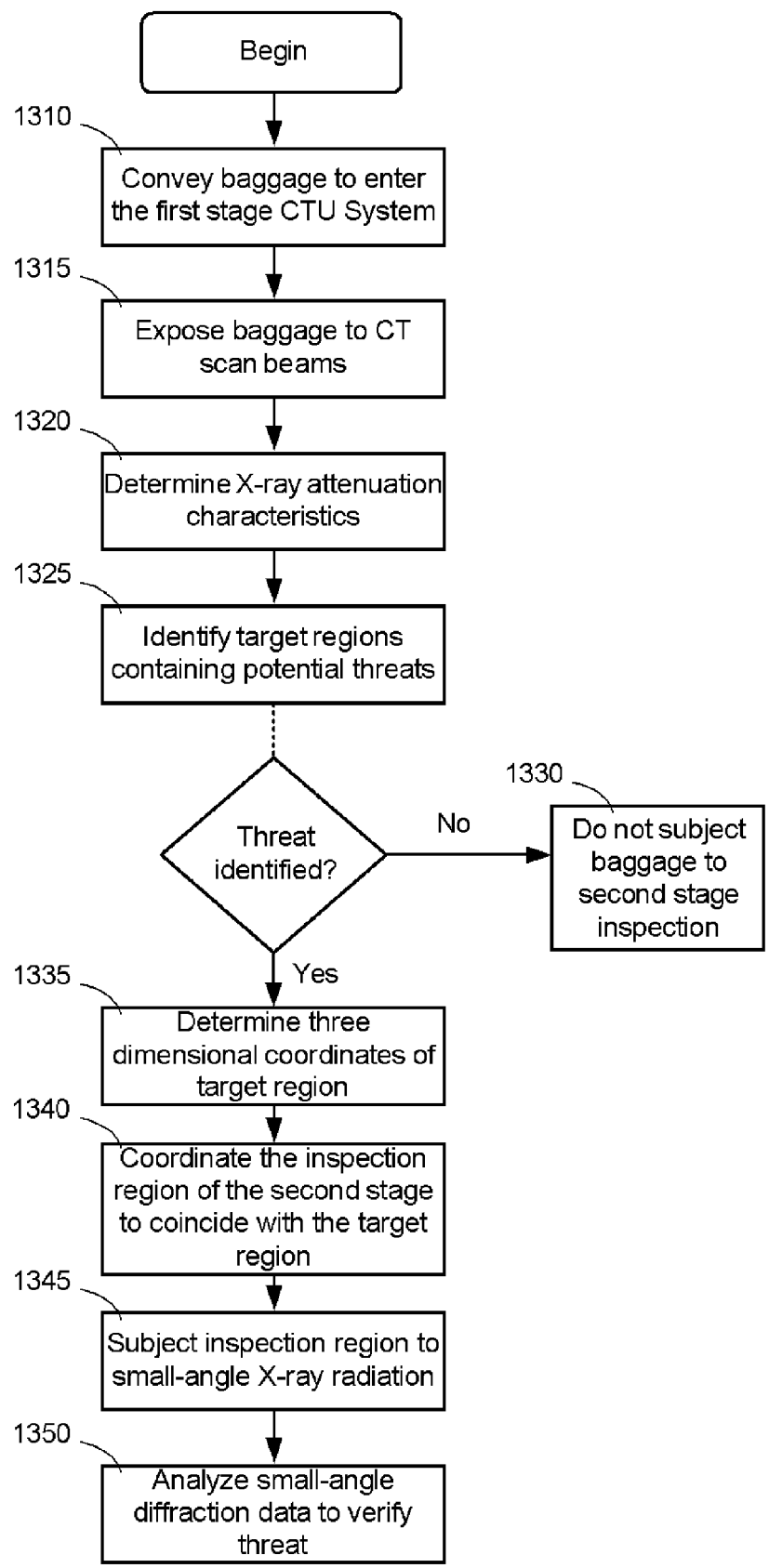
FIG. 13 is a flow diagram depicting another method of practicing the present invention.

FIG. 13 is a flow diagram of one exemplary operational process of the dual stage scanning system of the present invention. In step 1310, a piece of baggage is transported via conveyor belt system to enter into the first stage scan. In an exemplary embodiment, the first stage scan is a CT scanning system. In step 1315, the baggage is exposed to a plurality of projected beams from the CT scanner. From that exposure, X-ray characteristics are determined, in step 1320 and target regions containing potential threats are identified in step 1325. The CT Unit algorithms reconstruct the volume density distribution and store a copy of the data file for the required documentation. If there is a later need, the stored data files can be inspected by an operator. If no potential threats are identified, the container is not subjected to the second stage scan by the S-I Unit, as in step 1330.

If a potential threat alarm is triggered, the three dimensional coordinates of a target region is determined in step 1335. In step 1340, the inspection region generated by the second stage scanning system is coordinated to coincide with the target region. The inspection region is subjected to small angle X-ray radiation in order to obtain Bragg spectral data in step 1345. The spectral data is then analyzed, in step 1350, to verify and determine the existence of a threat. In a preferred embodiment, the second stage scanning system also employs certain three dimensional baggage data adjacent to the threats. From this additional data, the second stage system (here, a S-I scanning unit) can calculate beam hardening and spectral de-convolution functions for the actual diffraction beam path. The functions are then used to correct the measured diffraction spectrum, before it gets fed to a S-I Unit automatic threat resolution algorithm. It should be noted that the automatic threat resolution techniques described above can also be implemented in the present embodiment.

In the interest of maximizing throughput, both the first stage CT Unit and second stage S-I Unit are combined in such a way that any bag cleared by the first stage, therefore not requiring second stage inspection, is transported via an alternate path along the conveyor system (essentially removed from the path of the second stage), to prevent a decrease in throughput. Referring back to FIG. 1, the primary purpose of the LTS 141, 142 (collectively referred to hereinafter as LTS) is to handle all aspects of transporting luggage (such as baggage routing and baggage positioning in the SIU gantry) through the system 100, whether in a stand-alone or conveyor integrated (in-line) mode. The LTS comprise conveyor systems 121, 122 along with associated conventional motion control drives. The LTS is controlled and coordinated by programmable controllers such as computer systems 131, 132. As would be evident to persons of ordinary skill in the art, position sensors, positioning algorithm, detection algorithms, and other sources, like safety sensors, provide the input signals and commands required by the LTS.

The LTS aims at achieving a plurality of objectives such as keeping track of baggage when it arrives at the desired destination, ensuring that an alarmed bag can be made available for manual or second stage inspection at the earliest on-set of alarm, and keeping the inspection pipeline optimally filled and running. Also, in order to achieve improved throughput, both the first and second stages are preferably operated to be simultaneously active and do not have to "wait for each other" to complete their respective scanning stages.

Figure 14:
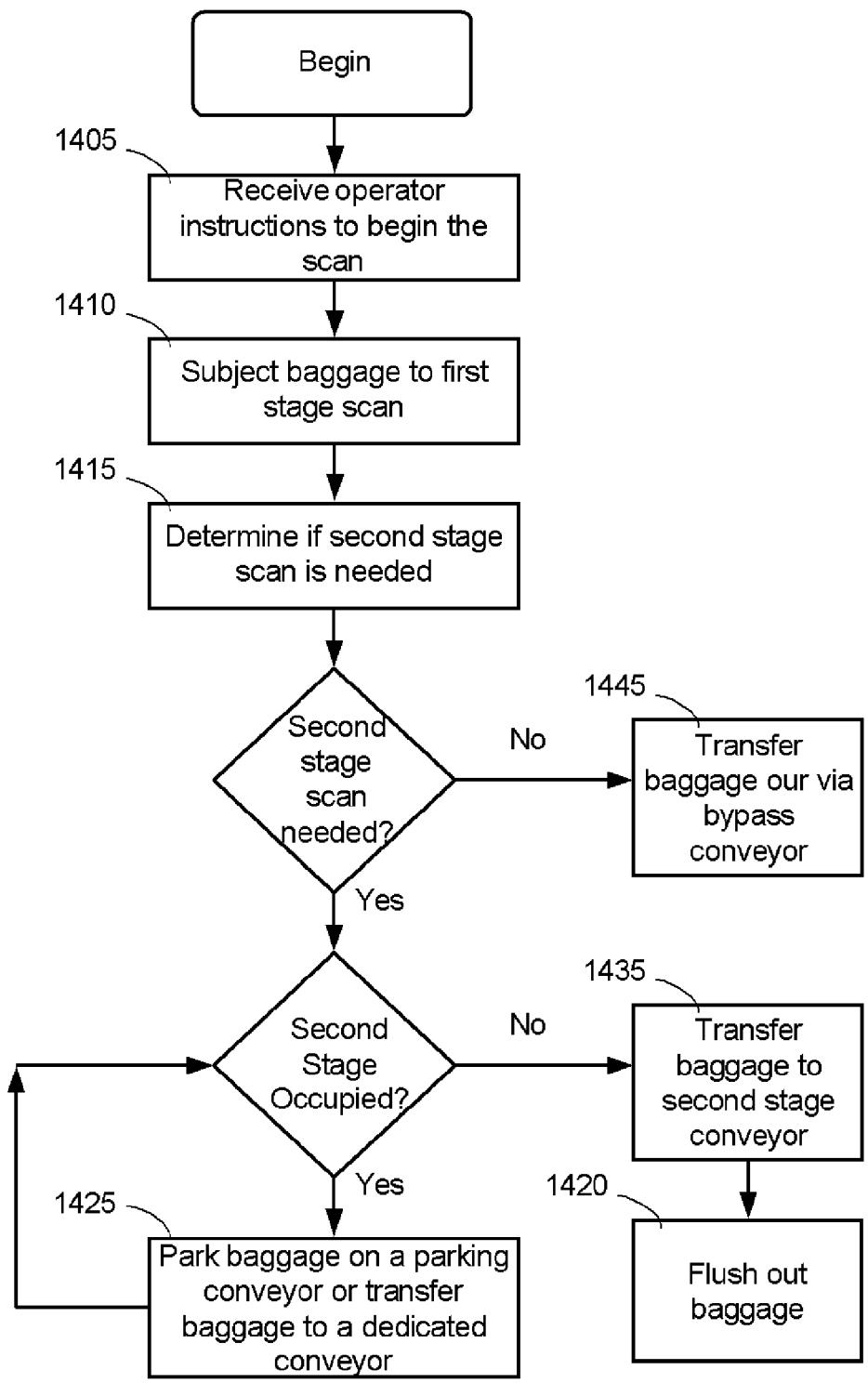
FIG. 14 is a flow diagram depicting another method of practicing the present invention.

FIG. 14 is a flow diagram of the process flow of one embodiment of the luggage transportation subsystem (LTS), as described above. In step 1405, the LTS receives instructions from an operator to start the scan. A piece of baggage is subjected to the first stage, CT Unit scan in step 1410. After the bag has been transported through the first stage Ct Unit, it is determined if further second stage inspection is required in step 1415. To achieve and maintain high levels of overall system throughput it is desirable to keep the number of alarms (generated in the first stage) sent to second stage inspections within appropriate limits. In one exemplary operational process, if a bag generates first stage alarms via use of the CT Unit, the LTS would require operator intervention. The operator could override the numerous first stage alarms and direct the S-I Unit to inspect a lesser number of typical locations in the second stage, after resolving other threat alarms based on an inspection of any of the three dimensional image map of the baggage generated in the first stage, manual inspection and/or other contextual details. The limit of the number of first stage alarms beyond which the LTS calls for operator intervention is predetermined and based upon past and real-time throughput data obtained from operating the combined scanning system.

If no further inspection is required, the bag is moved out through a second stage bypass in step 1445. If further inspection is required and the second stage is occupied, baggage is parked on a parking conveyor or transferred to a dedicate conveyor 1425. If further inspection is required and the second stage is not occupied, the baggage is transferred to the second stage conveyor in step 1435 and then out of the system upon scan completion 1420. This enables a quick turnaround for new baggage inspection in the first stage as well.

Also, while the first stage scans continually move baggage (at a certain speed) additional time is required for processes such as scanned slice reconstruction, automatic threat detection, and threat localization. During this further processing, the baggage is moved out from the first stage portion of the system and awaits a decision on whether the second stage scanning is required. If further scanning is required, the bag keeps moving undisturbed and is subsequently transferred to the S-I conveyor. The second stage conveyor is stopped at the leading threat location, enabling the S-I Unit signature or fingerprint to be obtained with the S-I unit gantry being simultaneously rotated to a proper azimuth. Subsequent similar stops may be necessary depending upon the number of first stage alarms to be resolved/verified. After second stage inspection, the baggage is released.

Alternative Second Stage, or Individual Stage, Screening System

The present embodiment is designed to better detect objects that are made from, but not limited to, special nuclear materials ("SNM") and/or high atomic number materials. The system employs advanced image processing techniques to analyze images of an object under inspection ("OUI"), which includes, but is not limited to baggage, parcels, vehicles and cargo and then alert the inspector, preferably with minimal human intervention, to the presence of these objects in the image. The inspector is then provided with a visual indication in the image of the presence, location, and configuration of the suspicious objects.

In one embodiment, the high-Z detection system of the present invention is implemented as a first or second stage within existing X-ray based detection systems. Using high-Z detection capability as a method for classifying high-Z regions of images enhances the throughput, detectability, and operational capability of current security screening systems.

In one embodiment, the present invention is directed towards a method for generating an image representation of high-atomic-number and special nuclear materials within objects under inspection using a radiation source, comprising generating an X-ray image using a radiographic inspection system; checking the image using an algorithm to clear or retain regions of objects based upon a threshold level; segmenting said image into regions based upon criteria; further inspecting regions that have not been cleared by using said algorithm to determine their size and shape; comparing said regions to threat criteria; and issuing an alarm to an inspector when a high-Z object is determined as suspicious in said comparing step.

In one embodiment, the present invention is directed toward an image analysis system and method for automatically detecting objects with high-atomic-number ("high-Z") materials or special nuclear material threats in radiographic images of baggage, parcels, and/or break bulk cargo without requiring additional imaging scans.

In one embodiment, the present invention is directed towards a method for generating both forward diffraction as well as fluorescence images of baggage, parcels, and/or break bulk cargo.

In one embodiment, the present invention is directed towards a method and system for classifying objects in a generated image of an object under inspection, identifying suspicious areas that may be special nuclear materials (SNM) or high-Z gamma-ray shielding, which could conceal radioactive materials or radiological dispersal devices (i.e. "dirty bombs").

In one embodiment, the present invention is directed towards an image analysis system and method for automatically detecting and classifying objects with high-atomic number (high-Z) materials or nuclear threats in radiographic images of vehicles and/or cargo, without requiring additional image scans.

In another embodiment, the present invention is directed towards a high energy portal X-ray inspection approach to enable a fast, accurate and efficient cargo scanning method, leading to increased threat detection and vehicle throughput. The present invention is designed to detect objects that are made from, but not limited to, special nuclear materials ("SNM") or gamma-ray shielding materials used to conceal radioactive materials or radiological dispersal devices (i.e. "dirty bombs"). The high-Z detection capability portal X-ray system is an enhanced radiographic system with improved image quality, image display, and automated image analysis.

In one embodiment, the portal X-ray inspection system of the present invention is deployed as a fixed (or stationary) system during inspection, allowing for better reliability, increased availability, and lower acquisition and operational costs. The high energy portal inspection system allows for high penetration and resolution enabling the effective and non-intrusive inspection of nearly all cargo, including dense loads.

In one embodiment, the high-Z detection system of the present invention is integrated with existing detection systems. In one embodiment, both the diffraction and fluorescence imaging stage are integrated as either a first or second stage of a conventional dual stage scanning system. The high-Z detection method and system of the present invention can be added to suitable X-ray imaging systems at low cost. In addition, multiple sources and/or detectors are not required on existing systems. The high-Z and special nuclear material detection and classification capability may be, in various alternative embodiments, incorporated into existing scanning systems, such as, but not limited to metal detectors, X-ray systems, baggage trace detectors, trace portals, personnel scanners, quadrupole resonance systems, X-ray diffraction systems, or personnel identification systems.

This high-Z detection process can be further generalized to accomplish the detection of other threats that may be hidden in bulk cargo. These include explosives, firearms, and other weapons of mass destruction. The use of neural-network classifiers may be used to assign a statistical probability that the suspicious area is a threat.

In one embodiment of the high-Z detection methods and systems of the present invention, the image data are automatically processed and an alarm given, for inspector resolution, if a high-Z material is determined to be present. Thus, it is not required that the inspector perceive a suspicious object in the image. This approach is complimentary to existing passive portal detectors.

Although the embodiments are described below in the context of exemplary baggage and cargo inspection system, it should be evident to persons of ordinary skill in the art that items other than luggage and cargo, such as but not limited to packages, mail, and cargo-containers, or even processed food stuffs, can also be analyzed and screened or graded and that the descriptions are exemplary and are not restrictive of the invention.

Reference will now be made in detail to specific embodiments of the invention. While the invention will be described in conjunction with specific embodiments, it is not intended to limit the invention to one embodiment.

I. High-Z Material Detection in Baggage, Parcels, and Hold Baggage

In one embodiment, the present invention is directed toward an image analysis system and method for automatically detecting objects with high-atomic-number ("high-Z") materials and/or special nuclear threat materials in radiographic images of baggage, parcels, and/or break bulk cargo without requiring additional imaging scans. In addition, the present invention is directed towards a method for generating both forward diffraction as well as fluorescence images of baggage, parcels, and/or break bulk cargo. In one embodiment, the diffraction and fluorescence imaging stage is integrated as a first or second stage of a conventional dual stage scanning system.

The present invention is also directed towards a method and system for classifying objects in a generated image of an object under inspection and identifying suspicious areas that may be special nuclear materials (SNM) or high-Z gamma-ray shielding, which could conceal radioactive materials or radiological dispersal devices (i.e. "dirty bombs").

FIG. 1 is a schematic illustration of one embodiment of exemplary baggage scanning system components of the present invention from both a functional and an operational perspective. Preferably, but not limited to such dimensions, the system of the present invention is designed such that it is able to handle suitcases, bags, parcels, and break bulk cargo up to 120 cm (length)×80 cm (width)×53 cm (height). When the conventional system finds an X-ray opaque ("high density") object in a bag, the system alarms, but no further information about the object is given. However, in one embodiment, the system of the present invention is quantitative, displaying an estimate of the mass, density, atomic number, and even the type of explosive or narcotics threat during the scanning process.

Thus, the systems and methods of the present invention enable further characterization of an opaque threat automatically by both declaring that a high atomic number ("high-Z") of special nuclear material is present and identifying the high-Z element or special nuclear material itself. The system of the present invention includes both the diffraction X-ray stage and an energy-dispersive detector system.

Figure 11:
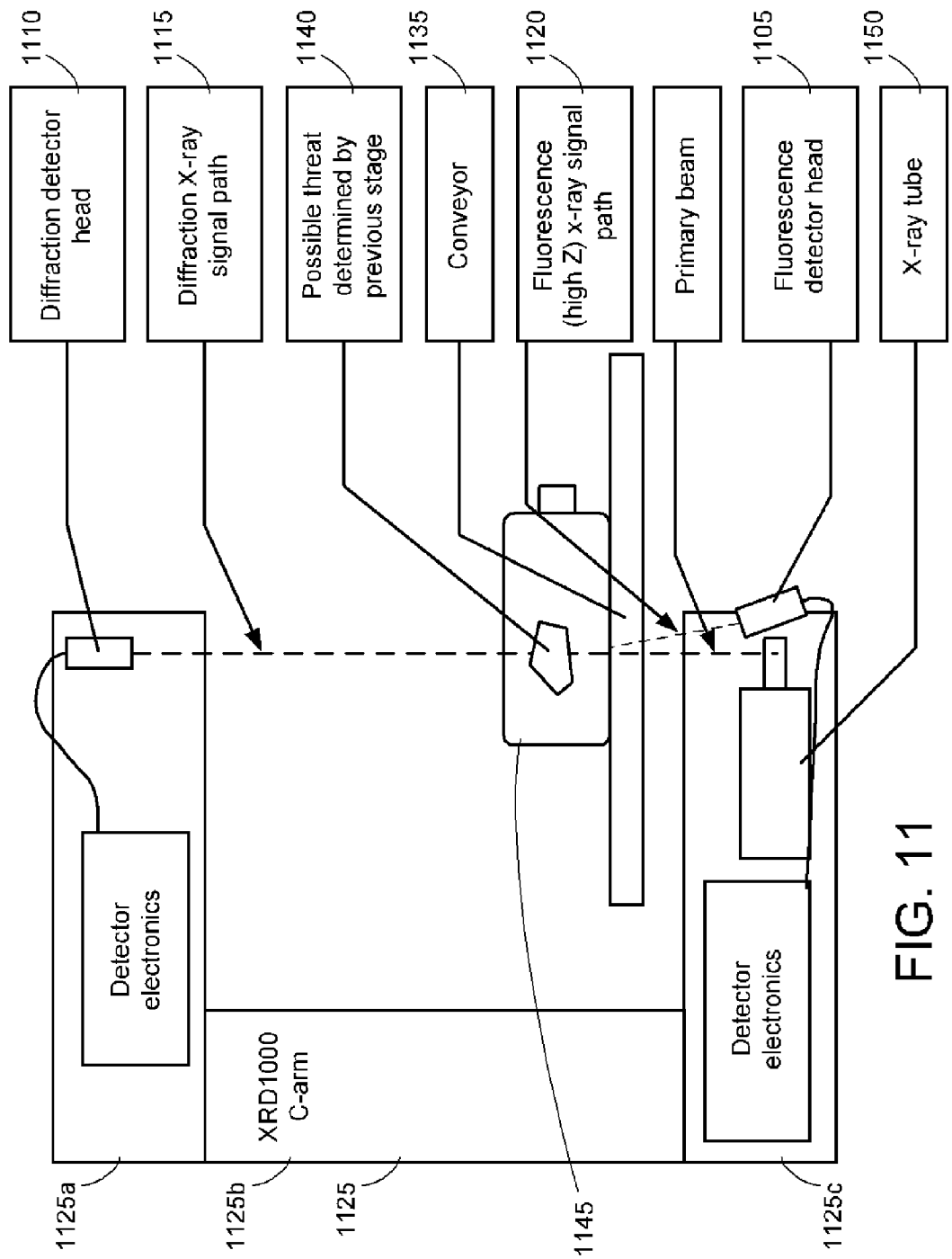
FIG. 11 is a schematic illustration of one embodiment of the system components having fluorescence detection.

Now referring to FIG. 11, the baggage scanning system of the present invention comprises fluorescence detector head 1105, which is mounted in a configuration that allows the recording of reflected X-ray spectrum 1120. In one embodiment, reflected X-ray spectrum 1120 is the fluorescence (high-Z) x-ray signal path. While reflected X-ray spectrum 1120 is being recorded, diffraction detector unit 1110 acquires a diffraction spectrum 1115 in the transmission direction. The X-rays that are transmitted from the primary beam after passing through the object under inspection are detected by diffraction detector unit 1110.

High-Z materials containing substances such as, but not limited to lead, tungsten, tantalum, gold, platinum, uranium, and plutonium add their distinctive K fluorescence line emissions (fluorescence peaks) to the spectrum, as described in greater detail below. The energy of fluorescence peaks of high-Z materials are high enough to be detectable outside a suitcase that they are hidden in.

In the high-Z detection capable baggage inspection system of the present invention, a large C-arm 1125 moves the diffraction camera across conveyor 1135, forming one of three motion controlled axes to locally address potential threats 1140 in object under inspection ("OUI") 1145. In one embodiment, OUI 1145 is a piece of baggage. C-arm 1125 is comprised of top section 1125a, which is fixedly attached in a perpendicular fashion to vertical section 1125b. Bottom section 1125c is fixedly attached to vertical section 1125b in a perpendicular fashion and is parallel to top section 1125a. Diffraction detector 1110, preferably a cadmium telluride detector, is located within top section 1125a of C-arm 1125. High brightness industrial X-ray tube 1150 is located within bottom section 1125c of C-arm 1125 and at least partially underneath conveyor 1135. By using an energy dispersive detector/collimator system, the system is capable of using both the conventional X-ray diffraction function and the reflected fluorescence function to determine the nature of the high-Z material. Fluorescence detector head 1105 is located within bottom section 1125c of C-arm 1125, adjacent to X-ray tube 1150.

Figure 15:
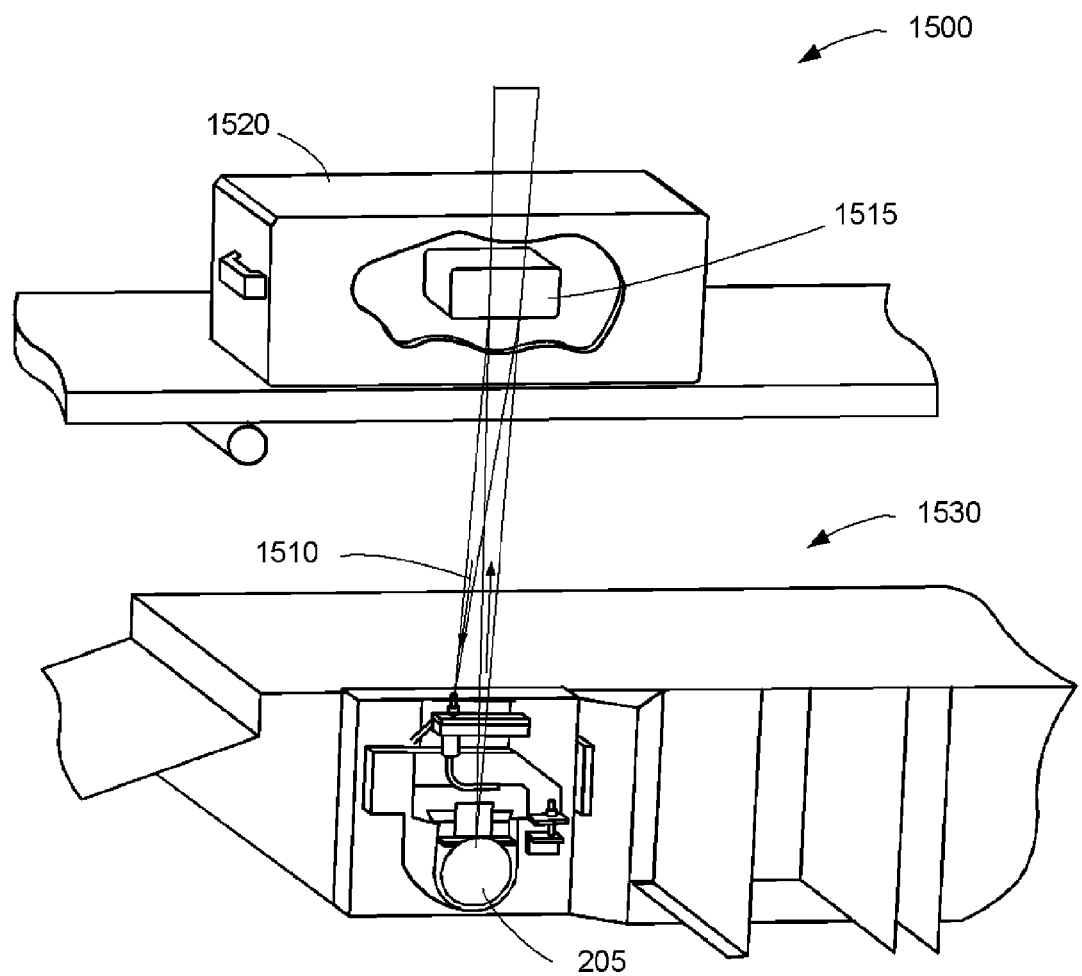
FIG. 15 is a detailed illustration of one embodiment of a baggage scanning system of the present invention, further depicting the X-ray tube and beam path.

FIG. 15 is a detailed illustration of one embodiment of a baggage scanning system of the present invention, further depicting the X-ray tube and beam paths. Referring now to FIG. 15 both the primary beam path 1510a (and later the transmitted beam path) and reflected fluorescence beam path 1510 are shown. Scanning system 1500 further comprises X-ray source 1505, which produces primary beam path 1530 to measure the transmitted X-ray diffraction pattern and reflected fluorescence beam path 1510 to measure the fluorescence from a potential threat target 1515 in an object under inspection 1520.

In one embodiment, as explained with respect to the prior embodiments, the detection system of the present invention operates automatically. Thus, the high-Z detection approach does not require that the inspector perceive a suspicious object in the image. Instead, the image data are automatically processed and an alarm given, for inspector resolution, if a high-Z material is determined to be present. This approach can be used as a compliment to existing passive radiation detectors.

In one threat detection system, such as in a dual stage scanning system, two projection scans of an object under inspection are taken. The scans are then analyzed for the presence of an explosive threat; if needed, the scans are also available for later alarm resolution by an operator. If a threat is suspected, the object under inspection proceeds on the conveyor to the second stage of the system where the diffraction spectrum at the threat location(s) determined in the first stage is taken. The spectra are automatically compared to the threat catalog, and an alarm is given when a match is found.

In one embodiment, the scanning system of the present invention comprises a fluorescence camera and high-Z threat alarm capability. Thus, the high-Z detection system of the present invention, is an enhanced radiographic system with improved image quality, image display, and automated image analysis. Using a high-Z detection methodology as a method for classifying high-Z regions of images enhances the throughput, detection capacity, and operational capability of inspection systems. As such, it decreases scan and display time for the images to substantially shorter than six seconds. In addition, the target throughput for fully automated inspection plus operator clearance is approximately 160 bags per hour.

In the first imaging stage, the system of the present invention automatically scans for the presence of highly attenuating metal parts. If detected, the object under inspection is automatically positioned in the diffraction stage. In the scanning system of the present invention, the diffraction stage is the combined diffraction and fluorescence stage, in which both the diffraction and fluorescence spectra are determined. If the primary beam hits a high-Z material hidden in the parcel, the reflected X-ray spectrum, containing the fluorescence signature of that target, will be recorded by the fluorescence detector. If the fluorescence spectrum contains a high-Z line, the system indicates an alarm and the threat location for explosives and/or high-Z threats are automatically indicated on the images.

In another embodiment, the scanning system of the present invention is in an operator interactive mode. Conventionally, in a dual stage scanning system, the operator can mark a location in the resultant X-ray images, whereupon the system can automatically check that location for the presence of a threat. With the added high-Z detection capability of the scanning system of the present invention, the operator can mark any location for testing for the presence of high-Z threat items.

As mentioned above, the fluorescent detection system of the present invention incorporates an energy dispersive detection system, which will readily pick up a large range of radioactive emissions. High-Z materials with an atomic number greater than 55 have fluorescence lines in the range of the energy dispersive detection system. Steel is a relatively low Z (26) material and does not, therefore, show fluorescence lines in the inspected energy range. The fluorescence signature is thus recognized when the high-Z threat is physically hidden or camouflaged by any material typically found in objects under inspection, such as, but not limited to baggage.

FIG. 16 is a table illustrating showing the K-shell fluorescence line energies in keV of a selection of different materials. Materials which can be reliably detected by the present invention, even in cluttered situations as is common in transport parcels, are listed in the table. The fluorescence signal reflected from a high-atomic-number metal or compound is very specific and thus, its spectral features are labeled as "simple".

Figure 17:
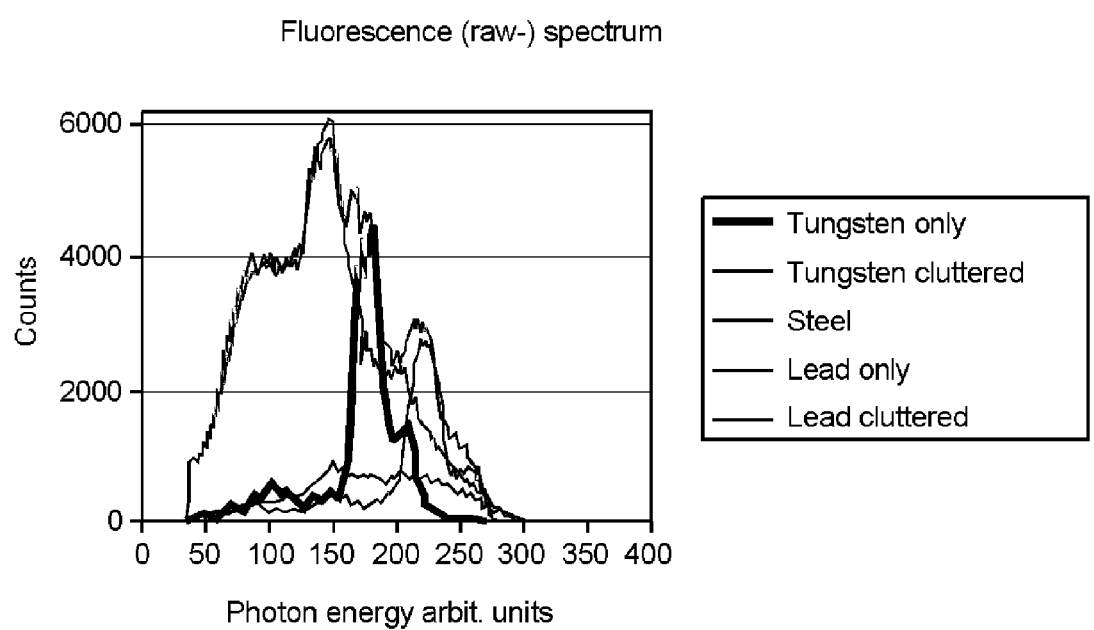
FIG. 17 is a graph depicting the "raw" fluorescence spectrum reflected from a high-atomic-number metal or compound.

FIG. 17 is a graph depicting the "raw" fluorescence spectrum reflected from a high-atomic-number metal or compound. As shown in FIG. 16, the spectrum resulting from a fluorescence signal is essentially a one or two line spectrum with a line position indicative of atomic number. In the case of when the object under inspection is a cluttered item, such as baggage, however, the exciting radiation as well as the reflected fluorescence radiation has to go through cluttering material, including suitcase walls and suitcase contents. As a consequence of the Compton scatter from the cluttering material, the specific fluorescence signal is distorted or corrupted. If the cluttering material is of low and/or medium atomic number (for example, iron), its fluorescence stays below the detection range of the system and will not be registered. The shape of Compton scatter contribution to the line spectrum (in the configuration employed) is in principle well known to those of ordinary skill in the art and will not be discussed in further detail here.

The system of the present invention identifies high-atomic-number ("high-Z") materials, including, but not limited to those associated with weapons of mass destruction, such as special nuclear materials (SNM). The algorithm employed in the system is based upon, among other characteristics, the ratio of the attenuation to the size of objects, thereby providing a method for identifying high-Z materials. The algorithm automatically processes radiographic images of objects under inspection to identify suspicious objects with these characteristic size-attenuation signatures of SNM.

The representative images used for detection in the scanning system of the present invention are, in part, obtained using a suitable industrial X-ray tube with the same distances and under similar scan conditions as conventional systems. Upon review of a database of over 2,000 images of like objects under inspection, characteristic features are extracted common to a given type of object under inspection. For example, but not limited to such example, a database may be based upon images of baggage. Characteristic features are then extracted based upon a common baggage type. Typical categories include: household goods, consumer goods, electronic components, clothes/apparel, books/paper other common personal, household, office items and various combinations of items typical of baggage, parcels, bulk break cargo or any other container as would be evident to persons of ordinary skill in the art.

Representative images obtained with other inspection systems, such as but not limited to gamma-ray (i.e. Co-60) and x-ray inspection systems are also examined in order to develop a list of features that characterize high-Z materials in these images. They are generally annotated with a description of the contents of the container—for example, some contain high-Z clutter, including PCs, laptops, PDAs, consumer electronics items and television Cathode Ray Tubes (CRTs), lead batteries, and other household and/or office supplies/equipment. While CRTs are readily identifiable in the image due to their distinctive shape, they will not be identified as suspicious high-Z objects by the image analysis techniques of the present invention. The glass used to form a CRT contains about 10% lead oxide and it will not produce the combination of attenuation, size, and other characteristics of special nuclear materials or shielding. This determines the effect on the ability to identify suspicious areas due to the penetration, resolution, dynamic range, and other operational parameters of these systems. This high-Z detection capability can be used to process images from a variety of inspection systems. The primary requirements are sufficient resolution to detect small quantities of high-Z materials and the penetration to image through the surrounding clutter.

Figure 18:
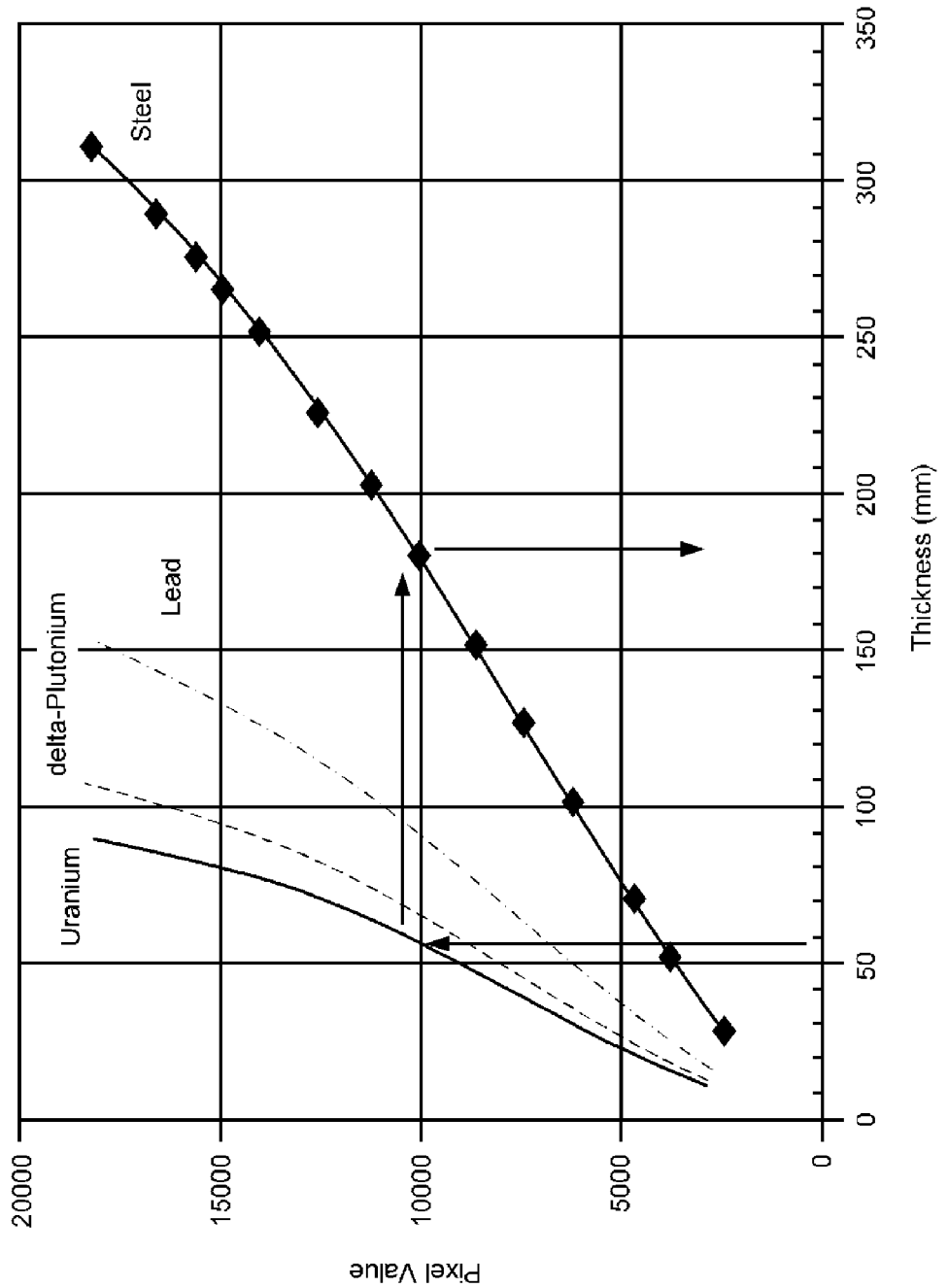
FIG. 18 is a graphical depiction of exemplary calibration curves for Uranium, Plutonium, Lead, and Steel relating material thickness to the attenuation (pixel) value.

FIG. 18 is a graphical depiction of exemplary calibration curves for uranium, plutonium, lead, and steel relating material thickness to the attenuation (pixel) value. Thus, the attenuation measured in the image, described by the pixel value, is converted to a material thickness. These calibration curves are derived from measurements of the attenuation produced by steel step-wedges using an industrial X-ray tube and can be used to illustrate how high-Z areas can be automatically identified within an image.

For example, but not limited to such example, assuming a 2-kg mass of a special nuclear material, the corresponding volume of 100 $cm^3$ (2-kg) is equivalent to a uranium sphere with a diameter of 58 mm. This hypothetical uranium sphere correlates to a pixel value of about 11,000 (shown on the graph using an upward pointing arrow), which further corresponds to a steel sphere of approximately 180 mm in diameter. This is shown on FIG. 18 as a right pointing and subsequently downward pointing arrow. Thus, if this sphere is made up of uranium, then it would have pixel attenuation values that are equivalent to approximately 180 mm of steel. The size and resulting attenuation of the object provide a characteristic indication of high-Z materials. Therefore, objects in the image that have a lateral dimension of 60 mm and the equivalent attenuation of about 180 mm of steel are regarded as suspicious.

A similar situation exists for a sphere of delta-phase plutonium alloy (density of 15.9 g/cm$^3$), as can be seen from the delta-Plutonium curve in FIG. 18. The discrimination problem is easier for low-Z clutter materials, such as plastics, where it would take a material thickness of about 19 times larger, i.e. 1100 mm to produce the same attenuation as 2-kg of a special nuclear material. Due to their depth of penetration, however, high-energy x-ray inspection systems can easily detect a special nuclear material that is hidden within low-Z neutron shields. The high depth of penetration is a consequence of the high absorption of X-rays and gamma rays by special nuclear materials, such as lead and tungsten, due to their high atomic number and density.

The above examples are merely illustrative of the many applications of the system of present invention. Although only a few embodiments of the present invention have been described herein, it should be understood that the present invention might be embodied in many other specific forms without departing from the spirit or scope of the invention. For example, while dual-stage scanning systems have been described with reference to first stage scanning systems comprising a CT scanning system and complimentary second stage S-I Unit scanning systems, comprising a transmission and scatter scan, other modifications and changes can be made by those of ordinary skill in the art. Additionally, while many of the systems described herein have been described with respect to use in dual stage scanning systems, it is to be understood that the embodiments described herein may be used as single stage scanning systems. Therefore, the present examples and embodiments are to be considered as illustrative and not restrictive, and the invention may be modified within the scope of the appended claims.

I claim:

1. An apparatus for inspecting an object, comprising:
a first stage inspection system comprising a conveyor for transporting the object into a first inspection volume, a dual energy X-ray source wherein said dual energy X-ray source is configured to irradiate said first inspection volume with dual energy radiation, and a detector array positioned opposite said dual energy X-ray source, configured to receive dual energy radiation transmitted through said object, and adapted to generate signals, comprising high energy data component and low energy data, based upon said received dual energy radiation; and
at least one processor for processing said signals to generate a three dimensional image of said object and to locate a threat within said object and for plotting said high energy data against said low energy data to identify at least one of spectra, parameters of analytical expressions, or spectral attenuation functions in a lookup table.

2. The apparatus of claim 1 wherein said first stage inspection system is adapted to identify a location of the threat within said object and to communicate said location to a human operator.

3. The apparatus of claim 1 wherein said first stage inspection system is adapted to identify a location of the threat within said object and to communicate said location to a second stage inspection system.

4. The apparatus of claim 3 wherein the second stage inspection system inspects said location to confirm the existence of said threat.

5. The apparatus of claim 3 wherein the second stage inspection system produces a second set of data having an X-ray signature characteristic of a material in said location.

6. The apparatus of claim 5 wherein the X-ray signature characteristic is at least one of mass, degree of attenuation, area, atomic number, size, shape, pattern, or context.

7. The apparatus of claim 3 wherein the second stage inspection system determines the existence of said threat by subjecting said object to radiation and detecting at least one of diffracted radiation or scattered radiation.

8. The apparatus of claim 7 wherein the second stage inspection system comprises a detector array having transmission detectors and energy-dispersive detectors.

9. The apparatus of claim 1 wherein said first stage inspection system is adapted to pass said object to a bypass conveyor when said processor determines that said object does not contain a threat.

10. The apparatus of claim 1 wherein said three dimensional image is generated by rotating said dual energy X-ray source and said detector array around said object.

11. The apparatus of claim 1 wherein said processor determines a location by analyzing the three dimensional image and determining a set of coordinates for the location based upon said three dimensional image.

12. The apparatus of claim 11 wherein said analysis comprises computing densities for a plurality of voxels within said three dimensional image.

13. The apparatus of claim 1 wherein said detector array comprises at least one first detector and at least one second detector, wherein said first detector is positioned in front of the second detector relative to a pathway of said transmitted dual energy radiation.

14. The apparatus of claim 13 wherein said first detector is configured to detect more lower energy photons than said second detector.

15. The apparatus of claim 14 wherein said second detector is configured to detect more higher energy photons than said first detector.

16. The apparatus of claim 1 wherein the processor processes said signals to discriminate between pairs of similar materials, wherein said pairs of similar materials comprises at least one pair selected from a) a plastic comprised of more oxygen and nitrogen atoms than hydrogen and carbon atoms and a plastic comprised of more hydrogen and carbon atoms than oxygen and nitrogen atoms and b) a material having more aluminum than steel and a material having more steel than aluminum.

17. An apparatus for inspecting an object, comprising:
a first stage inspection system comprising a conveyor for transporting the object into a first inspection volume, a dual energy X-ray source wherein said dual energy X-ray source is configured to irradiate said first inspection volume with dual energy radiation, and a detector array positioned opposite said dual energy X-ray source, configured to receive dual energy radiation transmitted through said object, and adapted to generate signals, comprising high energy data component and low energy data, based upon said received dual energy radiation;
at least one processor for processing said signals to generate a three dimensional image of said object, to locate a threat within said object, to generate a signal comprising data defining said location and to map said high energy data against said low energy data to identify at least one of spectra, parameters of analytical expressions, or spectral attenuation functions in a lookup table; and
a second stage inspection system comprising a radiation source and a detector array having at least one transmission detector or energy-dispersive detector, wherein said second stage inspection system inspects said object based on said location.

18. The apparatus of claim 17 wherein the second stage inspection system produces a second set of data having an X-ray signature characteristic of a material in said location, wherein the X-ray signature characteristic is at least one of mass, degree of attenuation, area, atomic number, size, shape, pattern, or context.

19. The apparatus of claim 17 wherein said detector array of the first stage inspection system comprises at least one first detector and at least one second detector, wherein said first detector is configured to detect more lower energy photons than said second detector, and wherein said second detector is configured to detect more higher energy photons than said first detector.

20. The apparatus of claim 19 wherein the processor processes said signals to discriminate between pairs of similar materials, wherein said pairs of similar materials comprises at least one pair selected from a) a plastic comprised of more oxygen and nitrogen atoms than hydrogen and carbon atoms and a plastic comprised of more hydrogen and carbon atoms than oxygen and nitrogen atoms and b) a material having more aluminum than steel and a material having more steel than aluminum.

* * * * *